(12) United States Patent
Fujii et al.

(10) Patent No.: US 8,460,915 B2
(45) Date of Patent: Jun. 11, 2013

(54) ESCHERICHIA COLI EXPRESSING THE CYTOCHROME P-450 GENE AND A METHOD FOR MICROBIAL CONVERSION USING THEM

(75) Inventors: Tadashi Fujii, Tokyo (JP); Yoshikazu Fujii, Tokyo (JP); Atsushi Ochiai, Tokyo (JP); Masashi Ito, Tokyo (JP); Kazuhiro Machida, Tokyo (JP)

(73) Assignee: Microbiopharm Japan Co., Ltd., Tokyo (JP)

( * ) Notice: Subject to any disclaimer, the term of this patent is extended or adjusted under 35 U.S.C. 154(b) by 400 days.

(21) Appl. No.: 12/449,876

(22) PCT Filed: Feb. 28, 2008

(86) PCT No.: PCT/JP2008/053563
§ 371 (c)(1),
(2), (4) Date: Dec. 7, 2009

(87) PCT Pub. No.: WO2008/105512
PCT Pub. Date: Sep. 4, 2008

(65) Prior Publication Data
US 2010/0285565 A1    Nov. 11, 2010

(30) Foreign Application Priority Data
Mar. 1, 2007    (JP) ................................ 2007-050936

(51) Int. Cl.
*C12N 9/00*     (2006.01)
*C12N 9/02*     (2006.01)
*C12N 1/20*     (2006.01)
*C12N 15/00*    (2006.01)
*C07H 21/04*    (2006.01)

(52) U.S. Cl.
USPC ..... 435/252.3; 435/183; 435/189; 435/320.1; 536/23.2

(58) Field of Classification Search
None
See application file for complete search history.

(56) References Cited

U.S. PATENT DOCUMENTS

| | | | | |
|---|---|---|---|---|
| 5,152,156 | A | 10/1992 | Tokairin | 62/498 |
| 2006/0234337 | A1 | 10/2006 | Arisawa et al. | |
| 2008/0220419 | A1 | 9/2008 | Kubota et al. | |

FOREIGN PATENT DOCUMENTS

| | | |
|---|---|---|
| EP | 0222109 A1 | 5/1987 |
| EP | 0724078 A1 | 7/1996 |
| EP | 0854293 A1 | 7/1998 |
| EP | 1 500 704 | 1/2005 |
| JP | 61-272492 | 12/1986 |
| JP | 4-241791 | 8/1992 |
| JP | 7-54782 | 2/1995 |
| JP | 07-067666 | 3/1995 |
| WO | WO 03/087381 | 10/2003 |
| WO | WO 2006/051729 | 5/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
European Search Report dated Nov. 17, 2009.
Takeda et al. "Isolation and identification of 2alpha, 25-dihydroxyvitamin D3, a new metabolite from *Pseudonocardia autotrophica* 100U-19 cells incubated with Vitamin D3" Steriods, vol. 71, No. 8, Aug. 1, 2006, pp. 736-744.
Sawada et al. "Conversion of vitamin D3 to 1alpha,25-dihydroxyvitamin D3 by *Streptomyces griseolus* cytochrome P450SU-1." Biochemical and Biophysical Research Communications, vol. 320, No. 1, Jul. 16, 2004, pp. 156-164.
Watanabe et al. "Cloning, characterization and expression of the gene encoding cytochrome P-450sca-2 from *Streptomyces carbophilus* involved in production of pravastatin, a specific HMG-CoA reductase inhibitor." Gene, vol. 163, No. 1, Sep. 22, 1995, pp. 81-85.
Ohta et al. "Production of human metabolites of cyclosporin A. AM1, AM4N and AM9, by microbial conversion." Journal of Bioscience and Bioengineering, vol. 99, No. 4, Apr. 1, 2005, pp. 390-395.
Sugano et al. "Cytochrome P-450-scc-catalyzed production of progesterone from cholestenone." Biochemistry and Molecular Biology International, vol. 35, No. 1, Jan. 1, 1995, pp. 31-36.
Yun et al. "Functional expression of human cytochrome P450 enzymes in *Escherichia coli*." Current Drug Metabolism, vol. 7, No. 4, May 1, 2006, pp. 411-429.
Fujii et al. "Efficient biotransformation using *Escherichia coli* with toIC acrAB mutations expressing cytochrome P450 genes." Bioscience Biotechnology and Biochemistry, vol. 73, No. 4, Apr. 1, 2009, pp. 805-810.
Fujii, T. (2006). Production of alpha, omega-alkanediols using *Escherichia coli* expressing a cytochrome P450 from *Acinetobacter* sp. OC4. *Biosci Biotechnol Biochem.*, 70, 1379-1385.
Maier, T. (2001). Molecular characterization of the 56-kDa CYP153 from *Acinetobacter* sp. EB104. *Biochem Biophys Res Commun.*, 286, 652-658.
Kagawa, N. (2003). Expression of human aromatase (CYP19) in *Escherichia coli* by N-terminal replacement and induction of cold stress response. *Steroids*, 68, 205-209.
Biosci Biotechnol Biochem. (2006) vol. 70, pp. 1379-1385.

* cited by examiner

*Primary Examiner* — Christian Fronda
(74) *Attorney, Agent, or Firm* — Jacobson Holman, PLLC

(57) ABSTRACT

Disclosed is a means for improving the poor conversion efficiency in a bioconversion system using an *Escherichia coli* cell having a bacterium-originated cytochrome P-450 gene integrated therein. A recombinant *Escherichia coli* cell is produced by introducing aciB and aciC which encode a gene for the electron transport system originated from the *Acinetobacter* sp. OC4 strain into an *Escherichia coli* cell, and adding a polynucleotide encoding an N-terminal sequence composed of 48 amino acid residues of AciA and the like to the 5'-terminus of a bacterium-originated cytochrome P-450 gene, wherein AciA is an alkane-oxidative cytochrome P-450 originated from the *Acinetobacter* sp. OC4 strain. Use of the recombinant *Escherichia coli* cell results in much effective microbial conversion of a hydrophobic or amphipathic substrate compound into a desired compound.

6 Claims, 1 Drawing Sheet

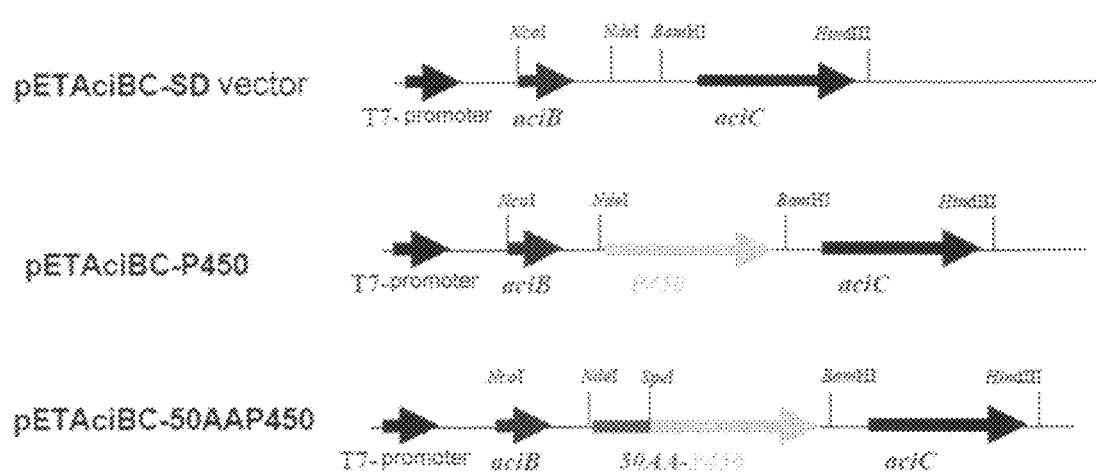

ESCHERICHIA COLI EXPRESSING THE CYTOCHROME P-450 GENE AND A METHOD FOR MICROBIAL CONVERSION USING THEM

CROSS-REFERENCE TO RELATED APPLICATIONS

This application is a 371 of PCT/JP08/053563 filed Feb. 28, 2008, which claims benefit of priority to Japanese Patent Application No. 2007-50936 filed on Mar. 1, 2007, which is expressly incorporated herein by reference in its entirety.

TECHNICAL FIELD

The present invention relates to transformed strains which are given by subjecting *Escherichia coli* to introduction of a cytochrome P-450 gene, a gene for the electron transport system or others which is originated from a xenogenic organism, and to a method for microbial conversion of a substrate compound using them.

BACKGROUND ART

In general, the means of producing compounds include chemical synthesis and enzymatic synthesis. In order to produce the compounds which can be materials for a variety of pharmaceutical products, it is essential to efficiently carry out regiospecific and stereospecific modifications of starting compounds. It is known that the enzymatic synthesis is superior in terms of these reactions.

In order to utilize an enzyme as a practical catalyst at an industrial level, however, the fundamental margin of the enzyme has to be considered. It comprises a short life span of the enzyme and the necessity of a coenzyme for catalytic events. Much attention has been paid so far to the way to elongate the life span of the enzyme and to retain the enzyme activity in the design for manufacturing processes with the enzyme. In addition, most enzymes used for the enzymatic synthesis require coenzymes in the catalytic events, and, for example, enzyme reactions for oxidation-reduction require a pyridine nucleotide such as NADH. These coenzymes are expensive in general, and therefore the addition of coenzyme has become an economically major issue when performing enzyme reactions at an industrial level.

As a solution to overcome of the margin of these enzyme reactions, a strategy using cells of a microorganism, particularly of *E. coli*, as a field for the enzyme reaction has been developed. That is, by means of transforming *E. coli* with an enzymatic gene, the target enzyme can be abundantly expressed within the cell. This means that the enzyme is continuously produced in the cell, and the enzyme activity can be retained as long as the cell is alive. Furthermore, a variety of intracellular reactions of metabolism enable the coenzymes required for the enzyme reactions to be regenerated.

An attempt has been made to produce the chemical substances which can be varieties of pharmaceutical materials by means of "microbial conversion" which comprises cultivating such a transformant of *E. coli* in a culture medium and bringing the culture contact with a substrate compound to obtain the modified compound. In particular, the oxidation reaction by microbial conversion of a hydrophobic or amphipathic compound using *E. coli* which has been transformed with a cytochrome P-450 gene has importance in pharmaceutical manufacturing.

On the other hand, a cytochrome P-450 enzyme which is encoded with a cytochrome P-450 gene (hereinafter also simply referred to as a P-450 enzyme) is the generic term for a group of the protoheme containing protein which is bound to carbon monoxide in its reduced form to give the soret band at around 450 nm. The P-450 enzyme is bound to tissues of most animals and plants, microsome of molds and yeasts and mitochondrial inner membrane of a part of animal tissues, and it exists in some kinds of bacteria and molds in its soluble form.

The P-450 enzymes have a variety of substrate specificity. There are enzymes exhibiting extraordinary wide substrate specificity which can utilize a large variety of organic compounds as the substrate, whereas some enzymes are found to have a rather strict substrate specificity which reacts only with comparatively limited kinds of organic compounds. Also some show excellent selectivity in stereo-specificity or regio-specificity to the reaction site. In addition, it is known that the P-450 enzymes are involved in, as specific functions, a wide variety of reactions such as xenobiotic hydroxylation, epoxidation, dealkylation and denitrogenation within the cells exhibiting the P-450 enzymes by catalyzing the monooxygenation.

In particular, a part of the P-450 enzymes originated from bacteria have practically been utilized for industrial production of useful compounds. One of the typical examples is the P-450 enzyme of *Storeptomyces carbophilus*, which hydroxylates the 6α-position of compactin, a substrate, to produce pravastatin as a product which is a therapeutic agent for hyperlipidemia (see Non Patent Literature 1). Furthermore, the method of producing active vitamin $D_3$ by hydroxylating the 1α-position and the 25-position of vitamin $D_3$ utilizing the P-450 enzyme of the *Pseudonocardia autotrophica* ATCC33795 strain, actinomycete, has been put to practical use. These P-450 enzymes originated from the bacteria can catalyze the monooxygenation only by conjugating with the electron transport system (ferredoxin and ferredoxin reductase) which donates electrons to the enzymes.

Such microbial conversion of compounds using cytochrome P-450 enzyme originated from bacteria has been performed by using a culture solution or bacterial body of the bacterium which was expressing the enzyme. In particular, with regard to the gene encoding the P-450 enzyme originated from actinomycetes, a culture solution has also been used which is given by introducing the said gene into *Storeptomyces lividans*, actinomycete, suitable as a host, and caused to express its enzyme activity. However, the microbial conversion of a substrate compound by an actinomycete having such a gene requires considerable time for culturing and converting the substrate compound into the objective product because of the unique nature of actinomycetes. In addition, depending upon the enzyme, investigation of the expression inducing conditions is required for effectively increasing the expression level of the enzyme. Furthermore, some actinomycetes used for the conversion have a reaction system which metabolizes or degrades the substrate compound or the objective product, and this contributes to generation of byproducts and decrease in the substrate compound and the objective product to lower the productivity of the objective product.

For these reasons, it has been desired to establish a system which can functionally express the cytochrome P-450 gene originated from bacteria (particularly the cytochrome P-450 gene originated from actinomycetes) and which uses as the host an *E. coli* requiring relatively short period of time for culture and also being considered to have less reaction systems to metabolize or degrade the substance compound and the objective product. As such a system, a system has been proposed that co-expresses the camAB gene encoding the electron transport system of P-450cam which is originated from *Pseudomonas putida* and causes to functionally express the cytochrome P-450 gene of a wide variety of actinomycetes (see Patent Document 1). However, the activity of microbial conversion by this system was quite low and inadequate to be utilized in industrial production.

On the other hand, it has been reported that the aciA gene which encodes the alkane oxydative P-450 enzyme belonging to the CYP153 family originated from the *Acinetobacter* sp. OC4 strain which belongs to bacteria and the gene group aciBC which encodes the electron transport system of the enzyme were caused to express in *E. coli.*, and the microbial conversion of n-octane was performed to accumulate about 2.2 g/L of 1-octanol in 24 hours (see Non Patent Literature 2). This production rate of 1-octanol is the maximum compared to those in the known microbial conversion, and this production rate was kept for 24 hours.

[Patent Literature 1] Brochure of International Publication No. 2003/087381, its family in English US 2006234337 A1

[Non Patent Literature 1] Cloning, characterization and expression of the gene encoding cytochrome P-450sca-2 from *Streptomyces carbophilus* involved in production of pravastatin, a specific HMG-CoA reductase inhibitor. Gene. 1995 Sep. 22; 163(1):81-85.

[Non Patent Literature 2] Production of alpha, omega-alkanediols using *Escherichia coli* expressing a cytochrome P450 from *Acinetobacter* sp. OC4. Biosci Biotechnol Biochem. 2006 June; 70(6):1379-1385.

[Non Patent Literature 3] Production of human metabolites of cyclosporin A, AM1, AM4N and AM9, by microbial conversion. J Biosci Bioeng. 2005 April; 99(4):390-395.

All the descriptions of the abovementioned Patent Literature 1 and Non Patent Literatures 1 to 3 are expressly incorporated herein by reference in their entirely.

The object of the present invention is to provide a means for improving the low conversion efficiency shown in the microbial conversion which uses the *E. coli.* introduced with a cytochrome P-450 gene originated from bacteria, especially from actinomycetes.

DISCLOSURE OF THE INVENTION

In order to achieve the aforementioned object, the present inventors made various further studies. As a result, they found that the substrate compound can be converted into its objective compound in great efficiency by inserting the gene group aciBC which encodes the electron transport system originated from the *Acinetobacter* sp. OC4 strain (NITE P-125), and also by adding the polynucleotide which encodes a polypeptide comprising the N-terminal 48 amino acid residues of AciA which is the alkane oxydative P-450 enzyme originated from the *Acinetobacter* sp. OC4 strain to the 5'-terminal of the cytochrome P-450 gene originated from bacteria to attain the present invention.

Thus, the present invention relates to the following [1] to [8].

[1] A transformant which is given by introducing aciB, aciC, and genes encoding a cytochrome P-450 enzyme originated from bacteria.

[2] The transformant according to [1] which is given by deleting the initiation codon at the 5'-terminal of the gene encoding the cytochrome P-450 enzyme originated from bacteria, and also adding a polynucleotide encoding the polypeptide according to SEQ ID No. 1 or its analogue to the 5'-terminal of the gene.

[3] The transformant according to [1] wherein the gene encoding the cytochrome P-450 enzyme is originated from actinomycetes.

[4] A plasmid in the autonomous replicating form or the integrated replicating form which carries aciB, aciC and genes encoding the cytochrome P-450 enzyme originated from bacteria.

[5] The plasmid according to [4] which is given by deleting the initiation codon at the 5'-terminal of the gene encoding the cytochrome P-450 enzyme originated from bacteria, and also adding a polynucleotide encoding the polypeptide according to SEQ ID No. 1 or its analogue to its 5'-terminal.

[6] The plasmid according to [4] or [5] wherein the gene encoding the cytochrome P-450 enzyme is originated from actinomycetes.

[7] A method for microbial conversion which uses the transformant according to any one of [1] to [3], characterized by performing monooxygenation of a substrate compound.

[8] The method according to [7] wherein the substrate compound is selected from the group consisting of vitamin $D_3$, 4-cholesten-3-one and cyclosporine.

Hereinafter the definition of the terms, symbols and so on described herein will be explained, and the present invention will be illustrated in detail. The term "aciB" used herein means the gene represented by the continuous nucleotide sequence starting from Nucleotide No. 1 to Nucleotide No. 321 in SEQ ID No. 2 which encodes ferredoxin originated from the *Acinetobacter* sp. OC4 strain, or its analogue.

The term "aciC" used herein means the gene represented by the continuous nucleotide sequence starting from Nucleotide No. 1978 to Nucleotide No. 3192 in SEQ ID No. 2 which encodes ferredoxin reductase originated from the *Acinetobacter* sp. OC4 strain, or its analogue.

The term "a transformant" used herein means a microorganism which is given by introducing into a specific microorganism a gene originated from another living organism in an expressible form by means of genetic recombination technologies, and the technique for gene transfer used for them includes not only the gene recombination using a vector such as plasmid but also homologous recombination and so on.

The term "method for microbial conversion" used herein means a method of culturing a transformant in a medium, bringing the culture into contact with a substrate compound, modifying the compound to convert into the objective compound, and obtaining it.

The term "microbial conversion" in the present invention means a reaction which comprises culturing a transformant in a medium, bringing the culture into contact with a substrate compound, and adding an oxygen atom to the compound.

The term "a substrate compound" used herein means a hydrophobic or amphipathic compound which has a carbon atom in its structure that can be subjected to monooxygenation by cytochrome P-450. For example, it includes alkane compounds such as hexane, heptane, octane and nonane, aromatic compounds such as toluene, phenol and cumene, steroids such as cholesterol, testosterone, 4-cholesten-3-one, dehydroepiandrosterone, vitamin $D_2$ and vitamin $D_3$, linear peptides such as leucyl-leucine, leucylvaline, polyleucine and polyvaline, diketopiperazines which are given by cyclocondensation of a dipeptide such as prolylphenylalanine and leucylalanine, cyclic peptides having physiological activity such as cyclosporine and echinomycin, monoterpenes such as pinene, camphene, limonene and geraniol, sesquiterpenes such as ambrosane, caryophyllane and drimane, diterpenes such as abietic acids and gibberellic acids, triterpenes such as dammarane, hopane and lanostane, statins such as compactin, macrolides such as tylosin, FK-506 and erythromycin, and also various kinds of drugs, or their precursors, metabolites, derivatives, and so on.

The term "a gene (polynucleotide) analogue" used herein means a polynucleotide which has substantially the same functions as the original gene (polynucleotide), and
(1) which hybridizes with the original gene (polynucleotide) under the stringent conditions,
(2) which has a nucleotide sequence having 70% or more homology with that of the original gene (polynucleotide),
(3) which has a nucleotide sequence complementary to that of the original gene (polynucleotide), or
(4) which does not hybridize with the original gene (polynucleotide) under the stringent conditions because of degeneracy of genetic codes, but which has a nucleotide sequence encoding the same sequence as the amino acid sequence encoded by the polynucleotide defined in any one of (1) to (3).

In addition, the term "a polynucleotide which hybridizes under the stringent conditions" means, for example, a polynucleotide obtained by using colony hybridization technique, plaque hybridization technique or southern hybridization method and so on in which the original gene (polynucleotide) is used as the probe, and in particular, it includes a polynucleotide which can be identified by performing hybridization with the filter which is fixed with a polynucleotide originated from a colony or plaque in the presence of 0.7 to 1.0M sodium chloride at 65° C., and then cleaning the filter with the SSC solution in 0.1 to 2 times the concentration (the composition of the SSC solution in 1 time the concentration is composed of 150 mM sodium chloride and 15 mM sodium citrate) under the condition of 65° C.

According to the present invention, an expression system which can efficiently express the cytochrome P-450 gene originated from bacteria, especially the cytochrome P-450 gene originated from actinomycetes, is provided, and by using the expression system, various kinds of substrate compounds can be subjected to reaction such as hydroxylation and efficiently converted into the objective compounds.

BEST MODE FOR CARRYING OUT THE INVENTION

Hereinafter, embodiments of the present invention will be described in detail.
(Preparation of Transformant)

According to the present invention, E. coli to be the host is not particularly limited. E. coli may be those which can be used for amplification of a vector such as plasmid and phage DNA, and of the inserted gene. For example, commercially available E. coli which is commonly used as a host in the recombinant DNA experiments using the host-vector system can be advantageously utilized. Into such a host E. coli, the aciB gene represented by the continuous base sequence starting from Nucleotide No. 1 to Nucleotide No. 321 in SEQ ID No. 2 which encodes ferredoxin originated from the Acinetobacter sp. OC4 strain, and the aciC gene represented by the continuous nucleotide sequence starting from Nucleotide No. 1978 to Nucleotide No. 3192 in SEQ ID No. 2 which encodes ferredoxin reductase originated from the same strain are incorporated to prepare a transformant.

The method for incorporating aciB and aciC into the host is not particularly limited, and for example, the genes can be inserted into an appropriate vector to be incorporated into the host by the protoplast method, or electroporation method. The kind of the vector which can be used is not particularly limited, and for example, autonomously-replicating vectors (e.g., plasmid etc.) may be used, or vectors which have been incorporated into genome of the host cell when being introduced into the host and is replicated together with the incorporated chromosome may also be used. The preferred examples include autonomously-replicating vectors pUC18, pKK223-3, pETduet-1 and so on. In expression vectors, the genes are functionally connected with elements which are essential for transcription (e.g., promoter etc.). Promoter is a DNA sequence which exhibits transcription activity in the host cell, and it can be selected appropriately from the known ones.

(Cytochrome P-450 Originated from Bacteria)

In the present invention, any cytochrome P-450 gene can be used as long as it is originated from bacteria and meets the object of the present invention, and especially, the cytochrome P-450 gene originated from actinomycetes can be preferably used. The cytochrome P-450 gene intended to be incorporated into the expression system of the present invention includes, but is not limited to, one with a function to catalyze the monooxygenation in which at least a part of the DNA sequence has been determined and the information of each sequence is available from the gene databases (EMBL and GenBank). Especially the cytochrome P-450s categorized into the CYP105 family and the CYP107 family are considered to be mostly involved in catabolism and presumed to be beneficial especially in microbial conversion.

Examples of the cytochrome P-450 gene originated from actinomycetes include the cytochrome P-450 gene involved in vercopeptin biosynthesis originated from *Actinomadura verrucosospora*, the cytochrome P-450 gene involved in rifamycin biosynthesis originated from *Amycolatopsis mediterranei*, the cytochrome P-450 gene involved in balhimycin biosynthesis originated from *Amycolatopsis mediterranei*, the cytochrome P-450 gene involved in terpentecin biosynthesis originated from *Kitasatospora griseospola*, the cytochrome P-450 gene involved in mycinamycin biosynthesis originated from *Micromonospora griseorubida*, the cytochrome P-450 gene involved in compactin hydroxylation originated from *Microtetraspora recticatena*, the cytochrome P-450 gene involved in piperidine and pyrrolidine degradation originated from *Mycobacterium smegmatis* mc2155, the cytochrome P-450 gene involved in polyketide antibiotic TA biosynthesis originated from *Myxococcus xanthus*, the cytochrome P-450 gene involved in vitamin $D_3$ hydroxylation originated from *Pseudonocardia autotrophica*, the cytochrome P-450 gene involved in degradation of thiocarbamate agrochemicals originated from *Rhodococcus erythropolis*, the cytochrome P-450 gene involved in synthesis of plant physiologically active substances originated from *Rhodococcus fascians* (D188), the cytochrome P-450 gene involved in degradation of ethyl tert-butyl ether originated from *Rhodococcus ruber*, the cytochrome P-450 gene involved in erythromycin hydroxylation originated from *Saccharopolyspora etythraea*, the cytochrome P-450 gene involved in thaxtomin A biosynthesis originated from *Streptomyces acidiscabies*, the cytochrome P-450 gene involved in nikkomycin biosynthesis originated from *Streptomyces ansochromogenes*, the cytochrome P-450 gene involved in oleandomycin biosynthesis originated from *Streptomyces antibioticus*, the cytochrome P-450 gene involved in Simocyclinone biosynthesis originated from *Streptomyces antibioticus*, the cytochrome P-450 gene involved in furan ring formation of avermectin originated from *Streptomyces avermitilis*, the cytochrome P-450 gene involved in oligomycin biosynthesis originated from *Streptomyces avermitilis*, the cytochrome P-450 gene involved in polyketide-4 biosynthesis originated from *Streptomyces avermitilis*, the cytochrome P-450 gene involved in polyketide-9 biosynthesis originated from *Streptomyces avermitilis*, the cytochrome P-450 gene involved in biosynthesis of the other types of polyketide originated from *Streptomyces avermitilis*, the cytochrome P-450 gene involved in polyenemacrolide biosynthesis originated from *Streptomyces avermitilis*, the cytochrome P-450 gene involved in Peptide 7 biosynthesis originated from *Streptomyces avermitilis*, the cytochrome P-450 gene involved in compactin hydroxylation originated from *Streptomyces carbophilus*, the cytochrome P-450 gene involved in Clavulanic acid biosynthesis originated from *Streptomyces clavuligerus*, the cytochrome P-450 gene involved in compactin hydroxylation originated from *Streptomyces fluvus*, the cytochrome P-450 gene involved in tylosin biosynthesis originated from *Streptomyces fradiae*, the cytochrome P-450 gene involved in degradation of sulfonylurea agrochemicals originated from *Streptomyces griseolus*, the cytochrome P-450 gene involved in degradation of sulfonylurea agrochemicals originated from *Streptomyces griseolus*, the cytochrome P-450 gene involved in rapamycin biosynthesis originated from *Streptomyces hygroscopicus*, the cytochrome P-450 gene involved in FK520 biosynthesis originated from *Streptomyces hygroscopicus* var *ascomyceticus*, the cytochrome P-450 gene involved in mitomycin biosynthesis originated from *Streptomyces lavendulae*, the cytochrome P-450 gene involved in complestatin biosynthesis originated from *Streptomyces lavendulae*, the cytochrome P-450 gene involved in enterocin biosynthesis originated from *Streptomyces maritimus*, the cytochrome P-450 gene involved in pimaricin biosynthesis originated from *Streptomyces natalensis*, the cytochrome P-450 gene involved in amphotericin biosynthesis originated from *Streptomyces nodosus*, the cytochrome P-450 gene involved in nogalamycin biosynthesis originated from *Streptomyces nogalater*, the cytochrome P-450 gene involved in nystatin biosynthesis originated from *Streptomyces noursei*, the cytochrome P-450 gene involved in daunorubicin hydroxylation originated from *Streptomyces peucetius*, the cytochrome P-450 gene involved in daunomycin hydroxylation originated from *Streptomyces peucetius* subsp. *caesius*, the cytochrome P-450 gene involved in coumermycin A1 biosynthesis originated from *Streptomyces rishiriensis* strain DSM40489, the cytochrome P-450 gene involved in FK-506 hydroxylation originated from *Streptomyces* sp., the cytochrome P-450 gene involved in novobiocin biosynthesis originated from *Streptomyces spheroids*, the cytochrome P-450 gene involved in nikkomycin biosynthesis originated from *Streptomyces tendae*, the cytochrome P-450 gene involved in carbomycin epoxidation originated from *Streptomyces thermotolerans*, and the cytochrome P-450 gene involved in pikromycin and methymycin biosynthesis originated from *Streptomyces venezuelae*.

Furthermore, in incorporating the aforementioned P-450 gene originated from actinomycetes into the aforementioned *E. coli* having aciB and aciC, by deleting the initiation codon at the 5'-terminal of the P-450 gene and also adding to the 5'-terminal the polynucleotide encoding the continuous polypeptide starting from Amino acid No. 1 to No. 50 of SEQ ID No. 1 or its analogue, the substrate compound can be converted into the objective compound much more efficiently. The polypeptide of SEQ ID No. 1 is a polypeptide consisting of 48 amino acids at the N-terminal part of AciA which is an alkane oxydative cytochrome P-450 enzyme originated from the *Acinetobacter* sp. OC4 strain, and 50 amino acids including Thr and Ser which are amino acids given by translation of the SpeI site.

(Cultivation of the Transformant)

The transformant thus prepared is cultured in an appropriate nutritive medium under the conditions to enable expression of the inserted gene, if needed, by addition of an inducer and so on. Such a nutritive medium consists of appropriate carbon sources, nitrogen sources, inorganic salts and natural organic nutrients and so on, and as the carbon sources, one or more kinds of glucose, fructose, glycerol, sorbitol, organic acids and so on can be used, and as the nitrogen sources, one or more kinds of compounds such as ammonia, urea, ammonium sulfate, ammonium nitrate and ammonium acetate can be used. As the inorganic salt, salts such as potassium phosphate, dipotassium phosphate, magnesium sulfate, manganese sulfate, and ferrous sulfate can be used. Moreover, as the natural organic nutrients which have a growth-promoting effect on the bacterium to be used, peptone, meat extract, yeast extract, corn steep liquor, casamino acid and so on can be used, and a small amount of vitamins and nucleic acids can be contained.

(Microbial Conversion Using the Transformant)

Then the bacterial body expressing these genes is brought into contact with the substrate compound to perform the conversion reaction. The temperature in the conversion reaction can appropriately be determined in view of the optimum temperature of the transformant. The reaction time can also be determined appropriately in view of the conversion into the objective compound (the progress degree of the reaction) and so on. For example, the reaction is preferably performed at 20 to 37° C. for 1-5 days. Moreover, the reaction mode may be batch type or continuous type, or the reaction can be performed in any style.

(Isolation and Purification of the Objective Product)

For the isolation and purification of the generated objective product, the isolation and purification methods generally used for isolating the microbial metabolite from its culture solution can be utilized. For example, they include any known methods such as organic solvent extraction using methanol, ethanol, acetone, butanol, ethyl acetate, buty acetate, chloroform, toluene and so on, adsorption-desorption treatment using hydrophobic adsorption resin such as Diaion HP-20, gel filtration chromatography using Sephadex LH-20 and so on, adsorption chromatography with active carbon, silica gel and so on, or adsorption-desorption treatment by thin layer chromatography, or high-performance liquid chromatography using a reverse-phase column, and others. However, the methods are not particularly limited to those mentioned here. By means of using these methods singularly or in combination in any order or repeatedly, the objective compound can be isolated and purified.

EXAMPLES

Hereinafter, the present invention will be explained in more detail with specific examples, but it is not intended to limit the present invention to these examples. The percentage (%) in the following examples indicates percent by weight in the explanation of the culture media, and percent by volume in that of the mobile phase of HPLC.

Example 1

Construction of Plasmid (1) pETAciBC-SD Vector

Hereinafter all the PCR reactions were carried out with KOD#PLUS-DNA polymerase (Toyobo Co., Ltd.). The plasmid pDoIABC (see Non Patent Literature 2) was treated with the restriction enzymes NcoI and BamHI to give a DNA fragment containing the aciB gene which encodes ferredoxin originated from the *Acinetobacter* sp. OC4 strain. This fragment was joined to the NcoI and BamHI sites of a *E. coli* plasmid vector, pETduet-1 (Novagen), by T4 DNA ligase to give Plasmid A. Moreover, PCR was carried out using Primer 1 (see SEQ ID No. 6) and Primer 2 (see SEQ ID No. 7), and pDolABC as a template to amplify the DNA fragment containing the gene aciC which encodes ferredoxin reductase originated from the *Acinetobacter* sp. OC4 strain, and the treatment was performed with the restriction enzymes BamHI and HindIII. This fragment was joined to the BamHI and HindIII sites of Plasmid A by T4 DNA ligase to give Plasmid B. Then, in order to eliminate the rear one of the two T7 promoters of Plasmid B, Plasmid B was treated with the restriction enzymes EcoRV and NotI, smoothed using BKL Kit (Takara Shuzo Co., Ltd.), and then joined by T4 DNA ligase to give Plasmid C. On the other hand, PCR was carried out using Primer 3 (see SEQ ID No. 8) and Primer 4 (see SEQ ID No. 9), and the genomic DNA of the *Pseudonocardia autotrophica* ATCC33795 strain as a template to amplify the DNA fragment to be the spacer DNA sequence, and the treatment was performed with the restriction enzymes Bg/II and BamHI. This fragment was joined to the Bg/II and BamHI sites of Plasmid C by T4 DNA ligase to give pETAciBC-SD vector.

(2) pETAciBC-50AABP195 PCR was carried out using Primer 5 (see SEQ ID No. 10) and Primer 6 (see SEQ ID No. 11), and the genomic DNA of the *Acinetobacter* sp. OC4 strain as a template to amplify the DNA fragment containing the DNA (the gene of from Nucleotide No. 398 to 1891 of SEQ ID No. 2) which encodes 48 amino acids at the N-terminal part of the alkane oxydative P-450 oxidative enzyme AciA originated from the *Acinetobacter* sp. OC4 strain, and the treatment was performed with the restriction enzymes NdeI and SpeI. On the other hand, PCR was carried out using the primer 7 (see SEQ ID No. 12) and the primer 8 (see SEQ ID No. 13), and the genomic DNA of the *Dactylosporangium variesporum* IFO14104 strain as a template to amplify the BP195 gene, and the treatment was performed with the restriction enzymes SpeI and BamHI. These DNA fragments were joined to the NdeI and BamHI sites of the pETAciBC-SD vector by T4 DNA ligase to give a plasmid, pETAciBC-50AABP195.

(3) pETAciBC-BP195

PCR was carried out using Primer 8 and Primer 9 (see SEQ ID No. 14), and the genomic DNA of the *Dactylosporangium variesporum* IFO14104 strain as a template to amplify the BP195 gene having the function to hydroxylate the 25-position of vitamin $D_3$, and the treatment was performed with the restriction enzymes NdeI and BamHI. These DNA fragments were joined to the NdeI and BamHI sites of the pETAciBC-SD vector by T4 DNA ligase to give a plasmid, pETAciBC-BP195.

(4) pETAciBC-50AABP194

PCR was carried out using Primer 10 (see SEQ ID No. 15) and Primer 11 (see SEQ ID No. 16), and the genomic DNA of the *Dactylosporangium variesporum* IFO14104 strain as a template to amplify the BP194 gene having the function to hydroxylate the 25-position of vitamin $D_3$, and the treatment was performed with the restriction enzymes SpeI and BamHI. These DNA fragments were joined to the SpeI and BamHI sites of pETAciBC-50AABP195 by T4 DNA ligase to give a plasmid, pETAciBC-50AABP194.

(5) pETAciBC-BP195 PCR was carried out using Primer 11 and Primer 12 (see SEQ ID No. 17), and the genomic DNA of the *Dactylosporangium variesporum* IFO14104 strain as a template to amplify the BP194 gene having the function to hydroxylate the 25-position of vitamin $D_3$, and the treatment was performed with the restriction enzymes NdeI and BamHI. These DNA fragments were joined to the NdeI and BamHI sites of the pETAciBC-SD vector by T4 DNA ligase to give a plasmid, pETAciBC-BP194.

(6) pETAciBC-50AAvdh PCR was carried out using Primer 13 (see SEQ ID No. 18) and Primer 14 (see SEQ ID No. 19), and the genomic DNA of the *Pseudonocardia autotrophica* ATCC33795 strain as a template to amplify the vdh gene having the function to hydroxylate the 25-position of vitamin $D_3$, and the treatment was performed with the restriction enzymes SpeI and BglII. These DNA fragments were joined to the SpeI and BamHI sites of pETAciBC-50AABP195 by T4 DNA ligase to give a plasmid, pETAciBC-50AAvdh.

(7) pETAciBC-vdh

PCR was carried out using Primer 14 and Primer 15 (see SEQ ID No. 20), and the genomic DNA of the *Pseudonocardia autotrophica* ATCC33795 strain as a template to amplify the vdh gene having the function to hydroxylate the 25-position of vitamin $D_3$, and the treatment was performed with the restriction enzymes NdeI and BglII. These DNA fragments were joined to the NdeI and BamHI sites of pETAciBC-50AAdvbA by T4 DNA ligase to give a plasmid, pETAciBC-vdh.

(8) pETcamAB-vdh

PCR was carried out using Primer 16 (see SEQ ID No. 21) and Primer 17 (see SEQ ID No. 22), and the genomic DNA of the *Pseudonocardia autotrophica* ATCC33795 strain as a template to amplify the vdh gene having the function to hydroxylate the 25-position of vitamin $D_3$, and the treatment was performed with the restriction enzymes NdeI and SpeI. These DNA fragments were joined by T4 DNA ligase to the NdeI and SpeI sites of pT7NS-camAB which is a vector causing co-expression of ferredoxin reductase and ferredoxin originated from *Pseudomonas putida* (see Patent Literature 1) to give a plasmid, pETcamAB-vdh.

(9) pETcamAB-BP195 PCR was carried out using Primer 9 and Primer 18 (see SEQ ID No. 23), and the genomic DNA of the *Dactylosporangium variesporum* IFO14104 strain as a template to amplify the BP195 gene having the function to hydroxylate the 25-position of vitamin $D_3$ (see SEQ ID No. 4), and the treatment was performed with the restriction enzymes NdeI and SpeI. These DNA fragments were joined to the NdeI and SpeI sites of pT7NS-camAB by T4 DNA ligase to give a plasmid, pETcamAB-BP195.

(10) pETcamAB-BP194

PCR was carried out using Primer 12 and Primer 19 (see SEQ ID No. 24), and the genomic DNA of the *Dactylosporangium variesporum* IFO14104 strain as a template to amplify the BP194 gene having the function to hydroxylate the 25-position of vitamin $D_3$ (see SEQ ID No. 5), and the treatment was performed with the restriction enzymes NdeI and SpeI. These DNA fragments were joined to the NdeI and SpeI sites of pT7NS-camAB by T4 DNA ligase to give a plasmid, pETcamAB-BP194. The overviews of each plasmid shown in Example 1 are illustrated in FIG. 1.

Example 2

Microbial conversion from vitamin $D_3$ into 25-hydroxyvitamin $D_3$

Using the plasmid pETAciBC-50AAvdh, pETAciBC-vdh, pETcamAB-vdh, pETAciBC-50AABP195, pETAciBC-BP195, pETcamAB-BP195, pETAciBC-50AABP194, pET-AciBC-BP194 and pETcamAB-BP194 which were prepared in Example 1, the *E. coli* BL21star(DE3) (Invitogen) was transformed to give the strains which were, respectively, BLstar/50AAvdh, BLstar/vdh, BLstar/camvdh, BLstar/

50AABP195, BLstar/BP195, BLstar/camBP195, BLstar/50AABP194, BLstar/BP194 and BLstar/camBP194.

These strains were seeded in the M9SEED liquid medium (3.39% $Na_2HPO_4$, 1.5% $KH_2PO_4$, 0.25% calcium chloride, 0.5% ammonium chloride, 1% casamino acid, 0.002% thymine, 0.1 mM calcium chloride, 0.1 mM iron sulfate, 0.4% glucose, 0.001 mM magnesium chloride) containing sodium carbenicillin (100 μg/mL), and cultured with shaking at 220 rpm at 25° C. for 24 hours. This culture solution 200 μL was added to 25 mL of the M9Main liquid medium (3.39% $Na_2HPO_4$, 1.5% $KH_2PO_4$, 0.25% sodium chloride, 0.5% ammonium chloride, 1% casamino acid, 0.002% thymine, 0.1 mM calcium chloride, 0.1 mM iron sulfate, 80 μg/mL 5-aminolevulinic acid) containing sodium carbenicillin (100 μg/mL) and Overnight Express Autoinduction Systems (Novagen), and cultured with shaking at 220 rpm at 25° C. for 24 hours. The bacterial body was collected by centrifugation, and suspended in 5 mL of the CV2 buffer (50 mM potassium phosphate buffer, 2% glycerin, 50 μg/mL carbenicillin, 0.1M IPTG) to obtain the bacterial body suspension in the 5-times concentration to the culture solution. To 1 mL of this bacterial body suspension, 25 μL of 1% vitamin $D_3$ DMSO solution (the final concentration 250 μg/mL) and PMCD (the final concentration 0.75%) were added, and the resulting solution was cultured with shaking at 220 rpm at 28° C. for 24 hours.

Then, the reaction mixture was added with 2 mL of methanol, vortexed at room temperature for 10 minutes, and then subjected to centrifugation by the Eppendorf centrifuge at 3,500 rpm for 10 minutes, and the resulting supernatant was analyzed by HPLC to detect 25-hydroxyvitamin $D_3$ generated by hydroxylating the substrate vitamin $D_3$. The result was shown in Table 1. The term "Wlid P-450" in the table below means a P-450 enzyme in which the sequence obtained from a microorganism has not been modified, and the term "50 amino acids addition P-450" means a P-450 enzyme added with the polypeptide consisting of 50 amino acids illustrated in SEQ ID No. 1.

TABLE 1

| Type of P450 to be expressed | Electron transport system to be expressed | Accumulation amount of the 25-hydroxylated vitamin $D_3$ depending on the kind of P450 to be expressed (μg/mL) and (specific activity to camAB) | | |
|---|---|---|---|---|
| | | vdh | BP195 | BP194 |
| Wild P450 | camAB | 4.2 (1.0) | 0.9 (1.0) | 0.5 (1.0) |
| Wild P450 | aciBC | 21.8 (5.2) | 2.0 (2.2) | 1.8 (3.6) |
| 50 amino acids addition P450 | aciBC | 46.7 (11.1) | 13 (14.0) | 3.3 (6.6) |

The measurement conditions of HPLC were as follows:

| Analyzer: | Agilent 100 series | |
|---|---|---|
| Column: | J' sphere ODS-H80 (YMC, Inc.), 75 mm × 4.6 mm I.D. | |
| Mobile phase: | A; acetonitrile | |
| | B; ion-exchanged water | |
| Gradient time setting: | 0 minute | mobile phase A/B = 30:70 |
| | 13.00 minutes | mobile phase A/B = 30:70 |
| | 14.00 minutes | mobile phase A/B = 100:0 |
| | 21.00 minutes | mobile phase A/B = 100:0 |
| | 22.00 minutes | mobile phase A/B = 70:30 |
| | 25.00 minutes | mobile phase A/B = 70:30 |

| Flow rate: | 1.0 mL/minute | |
|---|---|---|
| Detection: | UV 265 nm | |
| Injection volume: | 10 μL | |
| Column temperature: | 40° C. | |
| Analysis time: | 25 minutes | |
| Retention time: | 25-hydroxyvitamin $D_3$ | 8.8 minutes |
| | Vitamin $D_3$ | 21.0 minutes |

As is obvious from Table 1, in the hydroxylation at the 25-position of vitamin $D_3$, in comparison with the case using the strain by the conventional method in which the wild vdh and camAB were expressed in the BL21star(DE3) strain, the accumulation amount of 25-hydroxyvitamin $D_3$ was improved to 5.2 times by replacing camAB with aciBC for the electron transport system, and to 11.1 times by additionally expressing the vdh added with the polynucleotide encoding the polypeptide according to SEQ ID No. 1. And, in comparison with the case using the strain in which the wild BP195 and camAB were expressed in the BL21star(DE3) strain, the accumulation amount of 25-hydroxyvitamin $D_3$ was improved to 2.2 times by replacing camAB with aciBC, and to 14.0 times by additionally expressing the BP195 added with the polynucleotide encoding the polypeptide according to SEQ ID No. 1. Similarly, in comparison with the case using the strain in which the wild BP194 and camAB were expressed in the BL21star(DE3) strain, the accumulation amount of 25-hydroxyvitamin $D_3$ was improved to 3.6 times by replacing camAB with aciBC, and to 6.6 times by additionally expressing the BP194 added with the polynucleotide encoding the polypeptide according to SEQ ID. No. 1.

Example 3

Microbial conversion from 4-cholesten-3-one into 25-hydroxy-4-cholesten-3-one

Using the aforementioned *E. coli* BLstar/50AABP195, BLstar/BP195 and BLstar/camBP195, the bacterial body suspension was prepared in the same manner as in the microbial conversion from vitamin $D_3$ into 25-hydroxybitamin $D_3$. To 1 mL of this bacterial body suspension, 25 μL of 1% 4-cholesten-3-one methanol solution (the final concentration 250 μg/mL) and PMCD (the final concentration 0.75%) were added, and the resulting solution was cultured with shaking at 220 rpm at 25° C. for 24 hours. Then, the reaction mixture was added with 2 mL of methanol, vortexed at room temperature for 10 minutes, and then subjected to centrifugation by the Eppendorf centrifuge at 3,500 rpm for 10 minutes, and the resulting supernatant was analyzed by HPLC to detect 25-hydroxy-4-cholesten-3-one generated by hydroxylating the substrate 4-cholesten-3-one. The result obtained was shown in Table 2 together with the data of a part of Example 2 and Example 4.

The measurement conditions of HPLC were as follows:

| Analyzer: | Agilent 100 series | |
|---|---|---|
| Column: | Inertsil ODS/3 50 mm × 4.6 mm I.D. | |
| Mobile phase: | A; acetonitrile | |
| | B; 0.85% aqueous phosphate solution | |
| Gradient time setting: | 0 minute | mobile phase A/B = 40:60 |
| | 5.00 minutes | mobile phase A/B = 100:0 |
| | 8.00 minutes | mobile phase A/B = 100:0 |
| | 8.30 minutes | mobile phase A/B = 40:60 |
| | 11.00 minutes | mobile phase A/B = 40:60 |

-continued

| | |
|---|---|
| Flow rate: | 1.2 mL/minute |
| Detection: | UV 235 nm |
| Injection volume: | 40 μL |
| Column temperature: | 40° C. |
| Analysis time: | 11 minutes |
| Retention time: | 25-hydroxy-4-cholesten-3-one 4.97 minutes |
| | 4-cholesten-3-one 7.45 minutes |

Example 4

Microbial Conversion from Cyclosporine A into AM1

Using the aforementioned E. coli BLstar/50AABP195, BLstar/BP195 and BLstar/camBP195, the bacterial body suspension was prepared in the same manner as in the microbial conversion from vitamin $D_3$ into 25-hydroxybitamin $D_3$. To 1 mL of this bacterial body suspension, 25 μL of 1% cyclosporine A DMSO solution (the final concentration 250 μg/mL) was added, and the resulting solution was cultured with shaking at 220 rpm at 28° C. for 24 hours. Then, the reaction mixture was added with 2 mL of methanol, vortexed at room temperature for 10 minutes, and then subjected to centrifugation by the Eppendorf centrifuge at 3,500 rpm for 10 minutes, and the resulting supernatant was analyzed by HPLC to detect AM1 (see Non Patent Literature 3) generated by hydroxylating the substrate cyclosporine A. The result obtained was shown in Table 2 together with the data of a part of Example 2 and Example 3.

TABLE 2

| | | Accumulation amount of the hydroxylated product depending on the kind of the substrate (μg/mL) and (specific activity to camAB) | | |
|---|---|---|---|---|
| Type of P450 to be expressed | Electron transport system to be expressed | vitamin $D_3$ | 4-cholesten-3-one | Cyclosporine A |
| Wild P450 | camAB | 0.9 (1.0) | 8.6 (1.0) | 1.4 (1.0) |
| Wild P450 | aciBC | 2.0 (2.2) | 13.9 (1.6) | 1.7 (1.2) |
| 50 amino acids addition P450 | aciBC | 13 (14.0) | 14.1 (1.6) | 11.7 (8.3) |

The measurement conditions of HPLC were as follows:

| | | |
|---|---|---|
| Analyzer: | Agilent 100 series | |
| Column: | Zorbax SB C-18 100 mm × 4.6 mm I.D. | |
| Mobile phase: | A; acetonitrile | |
| | B; water | |
| Gradient time setting: | 0 minute | mobile phase A/B = 50:50 |
| | 8.00 minutes | mobile phase A/B = 90:10 |
| | 8.30 minutes | mobile phase A/B = 50:50 |
| | 8.31 minutes | mobile phase A/B = 40:60 |
| | 10.00 minutes | mobile phase A/B = 40:60 |
| Flow rate: | 1.0 mL/minute | |
| Detection: | UV 215 nm | |
| Injection volume: | 40 μL | |
| Column temperature: | 80° C. | |
| Analysis time: | 10 minutes | |
| Retention time: | AM1 | 4.53 minutes |
| | Cyclosporine A | 6.47 minutes |

As is obvious from Table 2, in the hydroxylation reaction of kinds of compounds by using the cytochrome P-450 gene BP195 originated from *Dactylosporangium variesporum*, it could be confirmed that the accumulation amount of each hydroxylated product by the method according to the present invention increases not only for vitamin $D_3$ but also for the other substrates in comparison with the case using the strain in which the wild BP195 and camAB were expressed in the BL21star(DE3) strain according to the conventional method.

That is, in case of using 4-cholesten-3-one as the substrate, the accumulation amount of 25-hydroxy 4-cholesten-3-one in comparison with the case using the strain in which the wild BP195 and camAB in the BL21star(DE3) strain was improved to 1.6 times by replacing camAB with aciBC for the electron transport system or by expressing the BP195 added with the polynucleotide encoding the polypeptide according to SEQ ID. No. 1. And, in case of using cyclosporine A as the substrate, the accumulation amount of AM1 which is the hydroxylated product of cyclosporine was similarly improved to 1.2 times by replacing camAB with aciBC, and to 8.3 times by additionally expressing the BP195 added with the polynucleotide encoding the polypeptide according to SEQ ID No. 1.

[Industrial Applicability]

The present invention is useful in the compound manufacturing domain utilizing enzymatic synthesis.

BRIEF DESCRIPTION OF DRAWINGS

FIG. 1 is the schematic view of pETAciBC-plasmid.

The invention claimed is:

1. A transformant of *E. coli* into which a plasmid has been incorporated wherein the plasmid comprises (a) a nucleic acid sequence encoding polypeptide AciB of SEQ ID NO: 25, (b) a nucleic acid sequence encoding polypeptide AciC of SEQ ID NO: 26, (c) nucleic acid encoding an actinomycetes cytochrome P-450 enzyme, and (d) nucleic acid encoding polypeptide sequence SEQ ID NO: 1 at the 5'-terminal end of the gene encoding the actinomycetes cytochrome P-450 enzyme from which the initiation codon has been deleted.

2. A plasmid comprising (a) a nucleic acid sequence encoding polypeptide AciB of SEQ ID NO: 25, (b) a nucleic acid sequence encoding polypeptide AciC of SEQ ID NO: 26, (c) nucleic acid encoding an actinomycetes cytochrome P-450 enzyme, and (d) nucleic acid encoding polypeptide sequence SEQ ID NO: 1 at the 5'-terminal end of the gene encoding the actinomycetes cytochrome P-450 enzyme from which the initiation codon has been deleted.

3. A method for microbial conversion comprising monooxygenation of a substrate compound with the transformant of claim 1.

4. The method according to claim 3, wherein the substrate compound is selected from the group consisting of vitamin $D_3$, 4-cholesten-3-one, and cyclosporine.

5. The plasmid of claim 2 in integrated replicating form.

6. The transformant of claim 1 wherein the plasmid is in integrated replicating form.

* * * * *

SEQUENCE LISTING

```
<160> NUMBER OF SEQ ID NOS: 26

<210> SEQ ID NO 1
<211> LENGTH: 50
<212> TYPE: PRT
<213> ORGANISM: Acinetobacter sp. OC4

<400> SEQUENCE: 1

Met Asn Ser Val Ala Glu Ile Phe Glu Lys Ile Thr Gln Thr Val Thr
 1               5                  10                  15

Ser Thr Ala Ala Asp Val Ala Thr Thr Val Thr Asp Lys Val Lys Ser
            20                  25                  30

Asn Glu Gln Phe Gln Thr Gly Lys Gln Phe Leu His Gly Gln Val Thr
        35                  40                  45
```

Thr Ser
    50

<210> SEQ ID NO 2
<211> LENGTH: 3192
<212> TYPE: DNA
<213> ORGANISM: Acinetobacter sp. OC4
<220> FEATURE:
<221> NAME/KEY: CDS
<222> LOCATION: (1)..(318)
<223> OTHER INFORMATION: aciB
<220> FEATURE:
<221> NAME/KEY: CDS
<222> LOCATION: (398)..(1888)
<223> OTHER INFORMATION: aciA
<220> FEATURE:
<221> NAME/KEY: CDS
<222> LOCATION: (1978)..(3189)
<223> OTHER INFORMATION: aciC

<400> SEQUENCE: 2

```
atg ggc caa att aca ttt att gcc cac gat ggt gca caa acc agc gtt      48
Met Gly Gln Ile Thr Phe Ile Ala His Asp Gly Ala Gln Thr Ser Val
 1               5                  10                  15 gca atc gaa gcg ggt aag tca cta atg cag ttg gcg gtt gaa aac ggt      96
Ala Ile Glu Ala Gly Lys Ser Leu Met Gln Leu Ala Val Glu Asn Gly
             20                  25                  30 gtt gcc gga att gat ggg gat tgc ggt ggc gaa tgc gcc tgt ggt acc     144
Val Ala Gly Ile Asp Gly Asp Cys Gly Gly Glu Cys Ala Cys Gly Thr
         35                  40                  45 tgc cac gtg att gtc agt gct gag tgg tcg gat gtt gcg ggt acg gca     192
Cys His Val Ile Val Ser Ala Glu Trp Ser Asp Val Ala Gly Thr Ala
 50                  55                  60 caa gcg aat gag cag cag atg ttg gaa atg acc cca gag cgt gct gcc     240
Gln Ala Asn Glu Gln Gln Met Leu Glu Met Thr Pro Glu Arg Ala Ala
 65                  70                  75                  80 acc tca cgt ttg gcg tgt tgt atc caa gtg acc gat gca atg gat ggc     288
Thr Ser Arg Leu Ala Cys Cys Ile Gln Val Thr Asp Ala Met Asp Gly
                 85                  90                  95 atg acg gta cat ctg cct gag ttt cag atg taa cacgtcagct gtaacccagc   341
Met Thr Val His Leu Pro Glu Phe Gln Met
            100                 105 ggatcaaccg ccttaacaaa cacacctcgt caacgatgct cagtcaggag accatc       397 atg aac tca gtc gca gaa att ttt gag aaa ata acc caa act gtc acc     445
Met Asn Ser Val Ala Glu Ile Phe Glu Lys Ile Thr Gln Thr Val Thr
                    110                 115                 120 agc acc gct gca gac gta gca acc acg gtt acg gat aaa gtc aag tct     493
Ser Thr Ala Ala Asp Val Ala Thr Thr Val Thr Asp Lys Val Lys Ser
            125                 130                 135 aat gag cag ttt caa acg ggc aag cag ttt ttg cat ggt caa gtg acc     541
Asn Glu Gln Phe Gln Thr Gly Lys Gln Phe Leu His Gly Gln Val Thr
        140                 145                 150 cgt ttt gtc cca ttg cac acg cag gtt cgc ggc att cag tgg atg caa     589
Arg Phe Val Pro Leu His Thr Gln Val Arg Gly Ile Gln Trp Met Gln
155                 160                 165                 170 aaa gcc aaa ttc cgt gtg ttt aac gtg caa gaa ttt cct gca ttt atc     637
Lys Ala Lys Phe Arg Val Phe Asn Val Gln Glu Phe Pro Ala Phe Ile
                175                 180                 185 gag caa ccg att cca gaa gtt gca aca ctg gca ctt gct gag att gat     685
Glu Gln Pro Ile Pro Glu Val Ala Thr Leu Ala Leu Ala Glu Ile Asp
            190                 195                 200 gtt agc aac cca ttt tta tac aag caa aaa aaa tgg cag tct tac ttt     733
Val Ser Asn Pro Phe Leu Tyr Lys Gln Lys Lys Trp Gln Ser Tyr Phe
```

-continued

|     |     |     |     |     | 205 |     |     |     | 210 |     |     |     |     | 215 |     |      |
|-----|-----|-----|-----|-----|-----|-----|-----|-----|-----|-----|-----|-----|-----|-----|-----|------|

```
aag cgg ctg cgt gat gaa gca ccg gta cat tat caa gcc aac agt ccg      781
Lys Arg Leu Arg Asp Glu Ala Pro Val His Tyr Gln Ala Asn Ser Pro
220                 225                 230 ttt ggg gca ttt tgg tcg gtc acg cgt tac gat gat att gtc tat gtc      829
Phe Gly Ala Phe Trp Ser Val Thr Arg Tyr Asp Asp Ile Val Tyr Val
235                 240                 245                 250 gat aaa aat cat gag att ttt tca gct gaa cct gtg atc gcg att ggc      877
Asp Lys Asn His Glu Ile Phe Ser Ala Glu Pro Val Ile Ala Ile Gly
                255                 260                 265 aac acc cct cct ggg tta ggt gct gaa atg ttt att gca atg gac cca      925
Asn Thr Pro Pro Gly Leu Gly Ala Glu Met Phe Ile Ala Met Asp Pro
        270                 275                 280 ccc aag cac gat gtg cag cgg cag gcc gta cag gat gta gtc gca cca      973
Pro Lys His Asp Val Gln Arg Gln Ala Val Gln Asp Val Val Ala Pro
    285                 290                 295 aaa aat ctc aaa gag cta gag ggt ttg att cgg cta cgc gtg caa gag     1021
Lys Asn Leu Lys Glu Leu Glu Gly Leu Ile Arg Leu Arg Val Gln Glu
300                 305                 310 gtt ttg gat cag ttg cca acg gat cag ccg ttt gat tgg gtg cag aat     1069
Val Leu Asp Gln Leu Pro Thr Asp Gln Pro Phe Asp Trp Val Gln Asn
315                 320                 325                 330 gtt tcg att gag ctg aca gcc cgt atg ttg gca aca tta ttt gat ttc     1117
Val Ser Ile Glu Leu Thr Ala Arg Met Leu Ala Thr Leu Phe Asp Phe
                335                 340                 345 cca tac gaa aag cgg cac aaa ttg gtt gaa tgg tca gac ttg atg gct     1165
Pro Tyr Glu Lys Arg His Lys Leu Val Glu Trp Ser Asp Leu Met Ala
        350                 355                 360 ggc act gcg gag gcc aca ggt ggg aca gtg aca aat ttg gat gag att     1213
Gly Thr Ala Glu Ala Thr Gly Gly Thr Val Thr Asn Leu Asp Glu Ile
    365                 370                 375 ttt gat gca gca gtc gat gca gca aag cat ttt gcg gag tta tgg cat     1261
Phe Asp Ala Ala Val Asp Ala Ala Lys His Phe Ala Glu Leu Trp His
380                 385                 390 aga aaa gcc gca caa aaa tct gca ggc gct gaa atg ggc tat gat ttg     1309
Arg Lys Ala Ala Gln Lys Ser Ala Gly Ala Glu Met Gly Tyr Asp Leu
395                 400                 405                 410 atc agc ttg atg cag tca aac gaa gcg act aaa gac ctg att tat cgg     1357
Ile Ser Leu Met Gln Ser Asn Glu Ala Thr Lys Asp Leu Ile Tyr Arg
                415                 420                 425 ccg atg gag ttt atg ggc aat ttg gtc ttg cta att gtc ggc ggc aac     1405
Pro Met Glu Phe Met Gly Asn Leu Val Leu Leu Ile Val Gly Gly Asn
        430                 435                 440 gat acc aca cgc aac tcg atg acg ggt ggg gta tac gca ctt aac ctg     1453
Asp Thr Thr Arg Asn Ser Met Thr Gly Gly Val Tyr Ala Leu Asn Leu
    445                 450                 455 ttt cca aat gag ttc gtc aaa ctc aaa aac aat ccg agc ttg atc ccg     1501
Phe Pro Asn Glu Phe Val Lys Leu Lys Asn Asn Pro Ser Leu Ile Pro
460                 465                 470 aac atg gta tcc gaa att att cgc tgg caa acc ccg ctg gcc tat atg     1549
Asn Met Val Ser Glu Ile Ile Arg Trp Gln Thr Pro Leu Ala Tyr Met
475                 480                 485                 490 cgt cgg att gcc aag caa gat gta gag ctt aac ggt cag acc atc aaa     1597
Arg Arg Ile Ala Lys Gln Asp Val Glu Leu Asn Gly Gln Thr Ile Lys
                495                 500                 505 aaa ggc gac aag gtg gtg atg tgg tac gtt tct ggc aac cgc gat gag     1645
Lys Gly Asp Lys Val Val Met Trp Tyr Val Ser Gly Asn Arg Asp Glu
        510                 515                 520 cga gtg att gag cga cct gat gaa ttg atc att gat cgt aaa ggt gcg     1693
Arg Val Ile Glu Arg Pro Asp Glu Leu Ile Ile Asp Arg Lys Gly Ala
```

```
                525                 530                 535
cgt aat cat ctg tca ttt ggt ttt ggt gtg cat cgc tgt atg ggt aat    1741
Arg Asn His Leu Ser Phe Gly Phe Gly Val His Arg Cys Met Gly Asn
540                 545                 550 cgc ttg gcc gag atg cag ttg cga atc tta tgg gaa gag ctg ctt cag    1789
Arg Leu Ala Glu Met Gln Leu Arg Ile Leu Trp Glu Glu Leu Leu Gln
555                 560                 565                 570 cgt ttt gaa aat att gag gtt ttg ggt gag cca gaa att gtg caa tct    1837
Arg Phe Glu Asn Ile Glu Val Leu Gly Glu Pro Glu Ile Val Gln Ser
                575                 580                 585 aac ttt gtg cgc ggc tat gcc aag atg atg gtc aaa ctg act gcc aaa    1885
Asn Phe Val Arg Gly Tyr Ala Lys Met Met Val Lys Leu Thr Ala Lys
            590                 595                 600 gcg tag gtatcaaaat aggcgacaga ggcattttgc aactgtcgtc ggcaacgatt     1941
Ala
gatgctgtgc atcaaccatg aactgagtga attcat atg caa aca atc gtc atc att 1998
                                       Met Gln Thr Ile Val Ile Ile
                                           605                 610 ggc gca agt cat gct gcg gcg cag ttg gcg gca agt ctg cgg cca gat    2046
Gly Ala Ser His Ala Ala Ala Gln Leu Ala Ala Ser Leu Arg Pro Asp
                615                 620                 625 ggc tgg cag ggc gag att gtg gtg atc ggc gat gag ccg tat ttg ccg    2094
Gly Trp Gln Gly Glu Ile Val Val Ile Gly Asp Glu Pro Tyr Leu Pro
            630                 635                 640 tat cat cga ccg ccg ttg tcc aag acc ttt tta cgc ggt gca caa ctg    2142
Tyr His Arg Pro Pro Leu Ser Lys Thr Phe Leu Arg Gly Ala Gln Leu
        645                 650                 655 gtc gat gag tta ttg att cgg cca gcc gct ttt tat caa aaa aat cag    2190
Val Asp Glu Leu Leu Ile Arg Pro Ala Ala Phe Tyr Gln Lys Asn Gln
    660                 665                 670 atc gaa ttt cgg cac ggg cgg gtg gtt gcg att gat cgg gca gcg cgc    2238
Ile Glu Phe Arg His Gly Arg Val Val Ala Ile Asp Arg Ala Ala Arg
675                 680                 685                 690 agc gtg aca cta caa gat ggc agt acg ctt gcg tat gac cag ttg gcg    2286
Ser Val Thr Leu Gln Asp Gly Ser Thr Leu Ala Tyr Asp Gln Leu Ala
                695                 700                 705 ctg tgt acc ggt gca cga gtc agg acg gtg tcg ctg gct ggg tct gat    2334
Leu Cys Thr Gly Ala Arg Val Arg Thr Val Ser Leu Ala Gly Ser Asp
            710                 715                 720 ttg gca ggt gtg cat tat ctt aga aat atc agc gat gta cag gct atc    2382
Leu Ala Gly Val His Tyr Leu Arg Asn Ile Ser Asp Val Gln Ala Ile
        725                 730                 735 cag cca ttt gta caa ccc aac ggc aaa gca gtg gtg atc ggt ggt ggc    2430
Gln Pro Phe Val Gln Pro Asn Gly Lys Ala Val Val Ile Gly Gly Gly
    740                 745                 750 tat atc ggt ctt gaa aca gcc gcc gca ttg acc gag cag ggc atg cag    2478
Tyr Ile Gly Leu Glu Thr Ala Ala Ala Leu Thr Glu Gln Gly Met Gln
755                 760                 765                 770 gtg gtg gtc ttg gaa gcc gcc gag cgg att ttg cag cgg gta act gca    2526
Val Val Val Leu Glu Ala Ala Glu Arg Ile Leu Gln Arg Val Thr Ala
                775                 780                 785 ccg gaa gtg tcg gac ttt tat acg cgg att cat cgc gaa cag ggt gtg    2574
Pro Glu Val Ser Asp Phe Tyr Thr Arg Ile His Arg Glu Gln Gly Val
            790                 795                 800 acg att cat acc ggt gtg tcg gtc acg gcg atc acg ggt gag ggg cgg    2622
Thr Ile His Thr Gly Val Ser Val Thr Ala Ile Thr Gly Glu Gly Arg
        805                 810                 815 gcg cag gcg gtg ctg tgt gcc gat ggt tcg atg ttc gat gca gat ctg    2670
Ala Gln Ala Val Leu Cys Ala Asp Gly Ser Met Phe Asp Ala Asp Leu
    820                 825                 830
```

```
gtg atc atc ggg gtc ggg gtt gta ccg aat atc gag ttg gcg ctg gac    2718
Val Ile Ile Gly Val Gly Val Val Pro Asn Ile Glu Leu Ala Leu Asp
835                 840                 845                 850 gcg ggc ttg cag gtg gac aat ggt att gtg att gat gag tat tgc cga    2766
Ala Gly Leu Gln Val Asp Asn Gly Ile Val Ile Asp Glu Tyr Cys Arg
                855                 860                 865 acc agt gcg cca gag att gtg gcc atc ggg gat tgt gcc aat gcg ttt    2814
Thr Ser Ala Pro Glu Ile Val Ala Ile Gly Asp Cys Ala Asn Ala Phe
        870                 875                 880 aat ccg att tat cag cgg cgg atg cgc ttg gag tcg gta cca aac gcc    2862
Asn Pro Ile Tyr Gln Arg Arg Met Arg Leu Glu Ser Val Pro Asn Ala
885                 890                 895 aat gaa cag gcc aaa att gcc tcg gcg acc ttg tgt ggc tta cag cgg    2910
Asn Glu Gln Ala Lys Ile Ala Ser Ala Thr Leu Cys Gly Leu Gln Arg
900                 905                 910 acc tcg aag agt ttg cct tgg ttt tgg tca gat cag tat gat cta aag    2958
Thr Ser Lys Ser Leu Pro Trp Phe Trp Ser Asp Gln Tyr Asp Leu Lys
915                 920                 925                 930 ttg cag att gcg gga ctc agt cag ggg tat gat cag atc gtg att cgg    3006
Leu Gln Ile Ala Gly Leu Ser Gln Gly Tyr Asp Gln Ile Val Ile Arg
            935                 940                 945 ggt gat gtg cag caa agg cgt agc ttt gca gcg ttt tat ttg cag gcg    3054
Gly Asp Val Gln Gln Arg Arg Ser Phe Ala Ala Phe Tyr Leu Gln Ala
            950                 955                 960 ggt cgc ctg att gcg gcg gat tgt gtg aat cgt ccg cag gag ttt atg    3102
Gly Arg Leu Ile Ala Ala Asp Cys Val Asn Arg Pro Gln Glu Phe Met
        965                 970                 975 cta agc aaa aag ctg atc acg gct ggt acg gcg gtc gat cca ctg cgg    3150
Leu Ser Lys Lys Leu Ile Thr Ala Gly Thr Ala Val Asp Pro Leu Arg
980                 985                 990 ttg gcg gat gag tcg att gcg gta cag gcg ttg atg ggg tag            3192
Leu Ala Asp Glu Ser Ile Ala Val Gln Ala Leu Met Gly
995                 1000                1005

<210> SEQ ID NO 3
<211> LENGTH: 2011
<212> TYPE: DNA
<213> ORGANISM: Pseudonocardia autotrophica ATCC33795
<220> FEATURE:
<221> NAME/KEY: CDS
<222> LOCATION: (320)..(1528)
<223> OTHER INFORMATION: vdh

<400> SEQUENCE: 3
gcgctcgggc tggaccggat cggcgaggtg acgacgctgg ggctgcgctc ggtgcggacc     60
gcatgggccg ggctgcggac gttcgccccg accgggcccc ggtgctgggg ggagtggccc    120
gatcatcccg ggttccactt cgtcgccggc cagggtggat ccggtatcga gtcggctccg    180
gcgctggccg cgctggcagc gtcgatgatc gtcgggcggc cggcgcccgc cgatgtcgcg    240
ctcgatcccg ctgtgtgctc ggtcactcgt ctccggtgac gtaagcgcgc gcttacgtcg    300
cgctggcacg atggggccc atg gcg ctg acc acc acc ggc acc gag cag cac    352
                        Met Ala Leu Thr Thr Thr Gly Thr Glu Gln His
                         1               5                   10 gac ctg ttc tcg ggc acc ttc tgg cag aac ccg cat ccc gcc tac gcg    400
Asp Leu Phe Ser Gly Thr Phe Trp Gln Asn Pro His Pro Ala Tyr Ala
        15                  20                  25 gca ctc cgt gcc gag gat ccg gta cgc aag ctc gcg ctg ccg gac ggg    448
Ala Leu Arg Ala Glu Asp Pro Val Arg Lys Leu Ala Leu Pro Asp Gly
    30                  35                  40 ccg gtc tgg ctg ctc acc cgc tac gcc gac gtg cgc gag gcg ttc gtc    496
Pro Val Trp Leu Leu Thr Arg Tyr Ala Asp Val Arg Glu Ala Phe Val
```

```
                 45                  50                  55
gat ccg cgc ctg tcg aag gac tgg cgc cac acg ctg ccc gag gac cag      544
Asp Pro Arg Leu Ser Lys Asp Trp Arg His Thr Leu Pro Glu Asp Gln
 60                  65                  70                  75 cgg gcg gac atg ccg gcc acg ccg acg ccg atg atg atc ctg atg gat      592
Arg Ala Asp Met Pro Ala Thr Pro Thr Pro Met Met Ile Leu Met Asp
                 80                  85                  90 ccg ccg gat cac acc cgg ctg cgc aag ctg gtc ggc agg tcg ttc acc      640
Pro Pro Asp His Thr Arg Leu Arg Lys Leu Val Gly Arg Ser Phe Thr
             95                 100                 105 gtc cgc cgg atg aac gag ctg gag ccg cgg atc acc gag atc gcc gac      688
Val Arg Arg Met Asn Glu Leu Glu Pro Arg Ile Thr Glu Ile Ala Asp
         110                 115                 120 ggc ctg ctc gcc ggc ctg ccc acc gac ggc ccg gtc gac ctg atg cgc      736
Gly Leu Leu Ala Gly Leu Pro Thr Asp Gly Pro Val Asp Leu Met Arg
     125                 130                 135 gag tac gcg ttc cag atc ccg gta cag gtg atc tgc gag ctg ctc ggg      784
Glu Tyr Ala Phe Gln Ile Pro Val Gln Val Ile Cys Glu Leu Leu Gly
140                 145                 150                 155 gtg ccc gcc gag gac cgc gac gac ttc tcc gcg tgg tcg tcg gtg ctg      832
Val Pro Ala Glu Asp Arg Asp Asp Phe Ser Ala Trp Ser Ser Val Leu
                160                 165                 170 gtc gac gac tcg ccg gcc gac gac aag aac gcg gcc atg ggc aag ctg      880
Val Asp Asp Ser Pro Ala Asp Lys Asn Ala Ala Met Gly Lys Leu
             175                 180                 185 cac ggc tac ctg tcc gac ctg ctg gag cgc aag cgc acc gag ccc gac      928
His Gly Tyr Leu Ser Asp Leu Leu Glu Arg Lys Arg Thr Glu Pro Asp
         190                 195                 200 gac gcg ctg ttg tcg tcg ctg ctg gcg gtg tcc gac gag gac ggc gac      976
Asp Ala Leu Leu Ser Ser Leu Leu Ala Val Ser Asp Glu Asp Gly Asp
     205                 210                 215 cgg ctc tcc cag gag gag ctc gtc gcg atg gcg atg ctg ctg ctg atc     1024
Arg Leu Ser Gln Glu Glu Leu Val Ala Met Ala Met Leu Leu Leu Ile
220                 225                 230                 235 gcc ggg cac gag acg acg gtc aac ctg atc ggc aac ggc gtc ctc gcc     1072
Ala Gly His Glu Thr Thr Val Asn Leu Ile Gly Asn Gly Val Leu Ala
                240                 245                 250 ctg ctc acg cac ccc gac cag cgg aag ctg ctg gcc gag gac ccg tcg     1120
Leu Leu Thr His Pro Asp Gln Arg Lys Leu Leu Ala Glu Asp Pro Ser
             255                 260                 265 ctg atc agc tcg gcg gtc gag gag ttc ctg cgg ttc gac tct ccc gtc     1168
Leu Ile Ser Ser Ala Val Glu Glu Phe Leu Arg Phe Asp Ser Pro Val
         270                 275                 280 tcg cag gcc ccg atc cgg ttc acc gcg gag gac gtc acc tac tcc ggc     1216
Ser Gln Ala Pro Ile Arg Phe Thr Ala Glu Asp Val Thr Tyr Ser Gly
     285                 290                 295 gtg acc atc ccg gcc ggc gag atg gtc atg ctc ggg ctg gcc gcc gcc     1264
Val Thr Ile Pro Ala Gly Glu Met Val Met Leu Gly Leu Ala Ala Ala
300                 305                 310                 315 aac cgg gac gcc gac tgg atg ccc gag ccg gac cgg ctc gac atc acc     1312
Asn Arg Asp Ala Asp Trp Met Pro Glu Pro Asp Arg Leu Asp Ile Thr
                320                 325                 330 cgg gac gcc tcc ggc ggg gtg ttc ttc ggg cac ggc atc cac ttc tgc     1360
Arg Asp Ala Ser Gly Gly Val Phe Phe Gly His Gly Ile His Phe Cys
             335                 340                 345 ctc ggt gcc cag ctg gcc cgg ctg gag ggc cgg gtc gcg atc gga cgg     1408
Leu Gly Ala Gln Leu Ala Arg Leu Glu Gly Arg Val Ala Ile Gly Arg
         350                 355                 360 ctg ttc gcc gat cgc ccg gag ctg gcg ctc gcg gtc ggc ctc gac gag     1456
Leu Phe Ala Asp Arg Pro Glu Leu Ala Leu Ala Val Gly Leu Asp Glu
```

-continued

```
         365                 370                 375
ctg gtc tac cgg gag tcg acg ctg gtc cgg ggg ctg tcg agg atg ccg      1504
Leu Val Tyr Arg Glu Ser Thr Leu Val Arg Gly Leu Ser Arg Met Pro
380                 385                 390                 395 gtg acg atg ggg ccg cgc agc gcc tga tcccgttcgc ggacgggccg            1551
Val Thr Met Gly Pro Arg Ser Ala
                400 ggcggcccgt ccgcgagtac ggtcagccgc tcagtggtgc cccggtcttc tcccgcacct   1611 cgtcggcggt gacgccggga gcggtctcga ccagcgcgag gccgcccggg gtgacgtcga   1671 tgacggcgag atcggtgacg atccgggtga cgcagcccag cccggtgatg ggcaggctgc   1731 acgactcgac gatcttgggc gtgccgtcgc gggacacgtg gtccatcatc acgatgacgg   1791 tgcgggcgcc gtgcacgagg tcatcgcgc cgcccatccc cttgatcatc ttcccgggca    1851 cggcccagtt ggcgagatcg ccgttggcgg cgacctgcat gccgccgagc acggcgacgt   1911 cgagcttccc ggcgcggatc tgggcgaagc tgtccgagga gccgaagtag gcggcgccgt   1971 cgttgacggt gacggtctcc ttgcccgcgt tgatcaggtc                         2011
```

```
<210> SEQ ID NO 4
<211> LENGTH: 1203
<212> TYPE: DNA
<213> ORGANISM: Dactylosporangium variesporum IFO14104
<220> FEATURE:
<221> NAME/KEY: CDS
<222> LOCATION: (1)..(1200)
<223> OTHER INFORMATION: BP195

<400> SEQUENCE: 4
```

```
atg acc gaa acg ctg tac ccc gag ctg ccc acg act cgc agc tca ccg      48
Met Thr Glu Thr Leu Tyr Pro Glu Leu Pro Thr Thr Arg Ser Ser Pro
1               5                   10                  15 ctg gac ccg ccc gcg gaa ctg ggg gtg ttg cgc gag acc gaa ccc atc      96
Leu Asp Pro Pro Ala Glu Leu Gly Val Leu Arg Glu Thr Glu Pro Ile
            20                  25                  30 agc cgg ctg gcg ttc ccg gac ggc acc ctg ggg tgg ctg gtg acc agc     144
Ser Arg Leu Ala Phe Pro Asp Gly Thr Leu Gly Trp Leu Val Thr Ser
        35                  40                  45 cac gcg ctc gcg cgg gag gtg ctg gcc gac aac cgg ttc agc aac cgg     192
His Ala Leu Ala Arg Glu Val Leu Ala Asp Asn Arg Phe Ser Asn Arg
    50                  55                  60 gcc gag cta cag cac tcg ccg atc cgg gcg ggc ggc aaa ccc atc ccg     240
Ala Glu Leu Gln His Ser Pro Ile Arg Ala Gly Gly Lys Pro Ile Pro
65                  70                  75                  80 caa cag ccg ccg gcc aag ccc ggc atg ttc atc aac atg gac ggc cag     288
Gln Gln Pro Pro Ala Lys Pro Gly Met Phe Ile Asn Met Asp Gly Gln
                85                  90                  95 gag cac gcc aag tac cgg cgg ctg ctg acc ggc cag ttc acc gtc cgg     336
Glu His Ala Lys Tyr Arg Arg Leu Leu Thr Gly Gln Phe Thr Val Arg
            100                 105                 110 cgg atg aac cag ctc atc ccc cgg atc gag gcc atc gtg cgc gac cac     384
Arg Met Asn Gln Leu Ile Pro Arg Ile Glu Ala Ile Val Arg Asp His
        115                 120                 125 ctg gcc gac gtg cgg gca cag ggg ccg ggc gtc gac ctc gtg gag gcg     432
Leu Ala Asp Val Arg Ala Gln Gly Pro Gly Val Asp Leu Val Glu Ala
    130                 135                 140 ttc gcg ctg ccg gtg ccg tcg atg gtg atc tgc gag ctg ctg ggg gtg     480
Phe Ala Leu Pro Val Pro Ser Met Val Ile Cys Glu Leu Leu Gly Val
145                 150                 155                 160 tcc tac gag gag cgc gag tcg ttc cag cgg aac acg aag gcg ctg ttt     528
Ser Tyr Glu Glu Arg Glu Ser Phe Gln Arg Asn Thr Lys Ala Leu Phe
```

|     |     |     |     |     |     |     |     |     |     |     |     |      |
|-----|-----|-----|-----|-----|-----|-----|-----|-----|-----|-----|-----|------|
|     |     |     | 165 |     |     |     | 170 |     |     |     | 175 |      |
| cac | cct | gac | caa | gga | gtt | tcg | ccg | aga | tca | ggg | cgg | cct  | tcg | agc | gga | 576 |
| His | Pro | Asp | Gln | Gly | Val | Ser | Pro | Arg | Ser | Gly | Arg | Pro  | Ser | Ser | Gly |     |
|     |     |     | 180 |     |     |     | 185 |     |     |     | 190 |      |     |     |     |     |
| tcg | agg | act | ttc | gtc | gcg | gac | ctc | gtg | cgg | cgc | aag | cac  | gac | gag | ccg | 624 |
| Ser | Arg | Thr | Phe | Val | Ala | Asp | Leu | Val | Arg | Arg | Lys | His  | Asp | Glu | Pro |     |
|     |     |     | 195 |     |     |     | 200 |     |     |     | 205 |      |     |     |     |     |
| ggc | gac | gac | atg | ctc | acg | ggt | ctg | atc | cag | acc | ggc | gag  | ctg | acc | gac | 672 |
| Gly | Asp | Asp | Met | Leu | Thr | Gly | Leu | Ile | Gln | Thr | Gly | Glu  | Leu | Thr | Asp |     |
| 210 |     |     |     |     | 215 |     |     |     |     | 220 |     |      |     |     |     |     |
| gag | gaa | gtc | gcc | aac | atg | ggg | ctc | ctc | ctg | ctc | gtc | gcc  | ggc | cac | gag | 720 |
| Glu | Glu | Val | Ala | Asn | Met | Gly | Leu | Leu | Leu | Leu | Val | Ala  | Gly | His | Glu |     |
| 225 |     |     |     |     | 230 |     |     |     |     | 235 |     |      |     |     | 240 |     |
| acg | acc | gcg | aac | atg | ctc | ggc | atc | ggc | acg | ctc | acc | ctg  | ctc | ggc | cac | 768 |
| Thr | Thr | Ala | Asn | Met | Leu | Gly | Ile | Gly | Thr | Leu | Thr | Leu  | Leu | Gly | His |     |
|     |     |     |     | 245 |     |     |     |     | 250 |     |     |      |     | 255 |     |     |
| ccc | gag | cag | ctg | gcg | gcg | ctg | aag | gcc | gac | ccg | tcc | ttg  | atc | gac | aac | 816 |
| Pro | Glu | Gln | Leu | Ala | Ala | Leu | Lys | Ala | Asp | Pro | Ser | Leu  | Ile | Asp | Asn |     |
|     |     |     | 260 |     |     |     | 265 |     |     |     | 270 |      |     |     |     |     |
| acg | gtc | gag | gag | ctg | atg | cgg | tac | ctg | tcg | atc | gtc | cag  | ttc | ggc | gcg | 864 |
| Thr | Val | Glu | Glu | Leu | Met | Arg | Tyr | Leu | Ser | Ile | Val | Gln  | Phe | Gly | Ala |     |
|     |     | 275 |     |     |     |     | 280 |     |     |     |     | 285  |     |     |     |     |
| tcc | agg | gtc | gcc | ctg | gag | gac | gtg | gaa | ctg | ggc | ggg | gtc  | acc | gtc | aag | 912 |
| Ser | Arg | Val | Ala | Leu | Glu | Asp | Val | Glu | Leu | Gly | Gly | Val  | Thr | Val | Lys |     |
|     | 290 |     |     |     |     | 295 |     |     |     |     | 300 |      |     |     |     |     |
| gcg | ggc | gag | ccg | gtc | agc | atc | tcg | gtg | atg | gcc | gcc | aac  | cgc | gac | ccg | 960 |
| Ala | Gly | Glu | Pro | Val | Ser | Ile | Ser | Val | Met | Ala | Ala | Asn  | Arg | Asp | Pro |     |
| 305 |     |     |     |     | 310 |     |     |     |     | 315 |     |      |     |     | 320 |     |
| gcc | aag | ttc | gac | cgc | ccg | gag | gag | ttc | gac | atc | cac | cgg  | ccg | gcg | acc | 1008|
| Ala | Lys | Phe | Asp | Arg | Pro | Glu | Glu | Phe | Asp | Ile | His | Arg  | Pro | Ala | Thr |     |
|     |     |     |     | 325 |     |     |     |     | 330 |     |     |      |     | 335 |     |     |
| ggc | cac | gtg | gcc | ttc | ggg | cac | ggc | gtg | cac | cag | tgc | ctg  | ggc | cag | cag | 1056|
| Gly | His | Val | Ala | Phe | Gly | His | Gly | Val | His | Gln | Cys | Leu  | Gly | Gln | Gln |     |
|     |     |     | 340 |     |     |     | 345 |     |     |     | 350 |      |     |     |     |     |
| ttg | gcg | cgc | atc | gag | atg | cgc | gtg | ggg | ttc | aac | gcc | ctg  | ttc | cgc | gag | 1104|
| Leu | Ala | Arg | Ile | Glu | Met | Arg | Val | Gly | Phe | Asn | Ala | Leu  | Phe | Arg | Glu |     |
|     |     | 355 |     |     |     |     | 360 |     |     |     |     | 365  |     |     |     |     |
| ttc | ccg | gac | ctg | cgg | ctc | gcg | gtg | ccg | gcc | tcg | gag | gtg  | ccg | atg | agg | 1152|
| Phe | Pro | Asp | Leu | Arg | Leu | Ala | Val | Pro | Ala | Ser | Glu | Val  | Pro | Met | Arg |     |
|     | 370 |     |     |     |     | 375 |     |     |     |     | 380 |      |     |     |     |     |
| gac | gac | atg | gcc | atc | tac | ggc | gtg | cac | aag | ctg | ccg | gtg  | acg | ttc | tca | 1200|
| Asp | Asp | Met | Ala | Ile | Tyr | Gly | Val | His | Lys | Leu | Pro | Val  | Thr | Phe | Ser |     |
| 385 |     |     |     |     | 390 |     |     |     |     | 395 |     |      |     |     | 400 |     |
| tga |     |     |     |     |     |     |     |     |     |     |     |      |     |     |     | 1203|

```
<210> SEQ ID NO 5
<211> LENGTH: 1404
<212> TYPE: DNA
<213> ORGANISM: Dactylosporangium variesporum IFO14104
<220> FEATURE:
<221> NAME/KEY: CDS
<222> LOCATION: (1)..(1401)
<223> OTHER INFORMATION: BP194

<400> SEQUENCE: 5
```

|     |     |     |     |     |     |     |     |     |     |     |     |     |     |     |     |    |
|-----|-----|-----|-----|-----|-----|-----|-----|-----|-----|-----|-----|-----|-----|-----|-----|----|
| atg | aac | tca | gtc | gca | gaa | att | ttt | gag | aaa | ata | acc | caa | act | gtc | acc | 48 |
| Met | Asn | Ser | Val | Ala | Glu | Ile | Phe | Glu | Lys | Ile | Thr | Gln | Thr | Val | Thr |    |
| 1   |     |     |     | 5   |     |     |     |     | 10  |     |     |     |     | 15  |     |    |
| agc | acc | gct | gca | gac | gta | gca | acc | acg | gtt | acg | gat | aaa | gtc | aag | tct | 96 |
| Ser | Thr | Ala | Ala | Asp | Val | Ala | Thr | Thr | Val | Thr | Asp | Lys | Val | Lys | Ser |    |
|     |     | 20  |     |     |     |     | 25  |     |     |     |     | 30  |     |     |     |    |

-continued

| | | |
|---|---|---|
| aat gag cag ttt caa acg ggc aag cag ttt ttg cat ggt caa gtg acc<br>Asn Glu Gln Phe Gln Thr Gly Lys Gln Phe Leu His Gly Gln Val Thr<br>35  40  45 | 144 |
| act agt acc agc ccc acc ggt tcc cgg gga ccc agc cag gac cgc ctg<br>Thr Ser Thr Ser Pro Thr Gly Ser Arg Gly Pro Ser Gln Asp Arg Leu<br>50  55  60 | 192 |
| gcc ctg cgg ctg ccg gag tac acc gag cgc acc ccg ggt tgc ccg<br>Ala Leu Arg Leu Pro Pro Glu Tyr Thr Glu Arg Thr Pro Gly Cys Pro<br>65  70  75  80 | 240 |
| ttc gac ccg tcg acc cgc ctg acc cgg atg ggc gct gag ggc ccc gtc<br>Phe Asp Pro Ser Thr Arg Leu Thr Arg Met Gly Ala Glu Gly Pro Val<br>85  90  95 | 288 |
| cac cag gtg acc atg ggc gac ggc gac acc gcc tgg ctg atc acg ggc<br>His Gln Val Thr Met Gly Asp Gly Asp Thr Ala Trp Leu Ile Thr Gly<br>100  105  110 | 336 |
| cac gag gag gcc cgc gcg gtg ccg gcg gac ccg agg ttc agc tcg gac<br>His Glu Glu Ala Arg Ala Val Pro Ala Asp Pro Arg Phe Ser Ser Asp<br>115  120  125 | 384 |
| cgc ttc cgc agc gaa cga gtc ctg cgc aaa ctc ccc gag acg ctg cgg<br>Arg Phe Arg Ser Glu Arg Val Leu Arg Lys Leu Pro Glu Thr Leu Arg<br>130  135  140 | 432 |
| cag cgc atg acc gac ccg gcc gtc cgc gcg ggc aac ttc atc acc atg<br>Gln Arg Met Thr Asp Pro Ala Val Arg Ala Gly Asn Phe Ile Thr Met<br>145  150  155  160 | 480 |
| gac gcc ccg gag cac acc cgg tac cgc aag ctc ctg acc ggc cag ttc<br>Asp Ala Pro Glu His Thr Arg Tyr Arg Lys Leu Leu Thr Gly Gln Phe<br>165  170  175 | 528 |
| acc gtc cgc cgg atg cgc caa ctg acc ccg cgc atc cag gag atc gtc<br>Thr Val Arg Arg Met Arg Gln Leu Thr Pro Arg Ile Gln Glu Ile Val<br>180  185  190 | 576 |
| acc gag cac ctg gac gcc atg ctc gcg tcc ggc aac cgc gcc gac ctg<br>Thr Glu His Leu Asp Ala Met Leu Ala Ser Gly Asn Arg Ala Asp Leu<br>195  200  205 | 624 |
| gtg cag gcc ttc gcc ctc ccg gtg cct tct ctg gtg atc tgc gaa ctc<br>Val Gln Ala Phe Ala Leu Pro Val Pro Ser Leu Val Ile Cys Glu Leu<br>210  215  220 | 672 |
| ctc ggc gtc gcc tac gag gac cgg gcc cag ttc cag gaa cgg tcc ggc<br>Leu Gly Val Ala Tyr Glu Asp Arg Ala Gln Phe Gln Glu Arg Ser Gly<br>225  230  235  240 | 720 |
| acc ctc ctg cgc ctc aac gcc ccg gcc gag gac gtg gtg aag gcc gcg<br>Thr Leu Leu Arg Leu Asn Ala Pro Ala Glu Asp Val Val Lys Ala Ala<br>245  250  255 | 768 |
| gac gaa ctg cgc gcc ttc atg cgc ggc ctc atc cgg tcc aag cgc gcc<br>Asp Glu Leu Arg Ala Phe Met Arg Gly Leu Ile Arg Ser Lys Arg Ala<br>260  265  270 | 816 |
| gag ccc acc gac gac ctc ctg tcg ggc ttg atc gcc tcc gca ccg gac<br>Glu Pro Thr Asp Asp Leu Leu Ser Gly Leu Ile Ala Ser Ala Pro Asp<br>275  280  285 | 864 |
| ctg acc gac gac gag ctg gtg gtg atc tcc ctg ctg ctg ttg atc gcc<br>Leu Thr Asp Asp Glu Leu Val Val Ile Ser Leu Leu Leu Leu Ile Ala<br>290  295  300 | 912 |
| ggc cac gag acc acg gcg aac atg ctc gcc ctg ggc acg ttc gcg ttg<br>Gly His Glu Thr Thr Ala Asn Met Leu Ala Leu Gly Thr Phe Ala Leu<br>305  310  315  320 | 960 |
| ctg gaa cac ccg gag gag ctc gcc aaa ctc cgc gac gac ccg tcc ctc<br>Leu Glu His Pro Glu Glu Leu Ala Lys Leu Arg Asp Asp Pro Ser Leu<br>325  330  335 | 1008 |
| atc gac ggg gcg gtg gag gag ctg ctg cgc tac ctg tcg atc gtc cac<br>Ile Asp Gly Ala Val Glu Glu Leu Leu Arg Tyr Leu Ser Ile Val His<br>340  345  350 | 1056 |

-continued

```
ctg ggg ccc gtg cgc acc acg ctg gag gag gtc gag atc gcc ggc gtc      1104
Leu Gly Pro Val Arg Thr Thr Leu Glu Glu Val Glu Ile Ala Gly Val
        355                 360                 365 cgc atc ccg gcc gac gaa acg gtg atc atc aac gtg ccg gtg gcc aac      1152
Arg Ile Pro Ala Asp Glu Thr Val Ile Ile Asn Val Pro Val Ala Asn
370                 375                 380 cgc gac cca cgg gtc tac ggc gac cgg gac cag ctg gac gtg gcc cgc      1200
Arg Asp Pro Arg Val Tyr Gly Asp Arg Asp Gln Leu Asp Val Ala Arg
385                 390                 395                 400 ggc cgg gtg tcc cac ctg gcg ttc ggg cac ggc atc cac cag tgc ctg      1248
Gly Arg Val Ser His Leu Ala Phe Gly His Gly Ile His Gln Cys Leu
                405                 410                 415 ggg cag cag ttg gcg cgg gtg gag atg gcc gtc ggg ttc acc gag ctg      1296
Gly Gln Gln Leu Ala Arg Val Glu Met Ala Val Gly Phe Thr Glu Leu
            420                 425                 430 ctg cgc cgg ctg ccg ggc ttg cgc ctg gac ctg ccg gct tcg gag gtc      1344
Leu Arg Arg Leu Pro Gly Leu Arg Leu Asp Leu Pro Ala Ser Glu Val
        435                 440                 445 ccg ctg cgc agc gac atg ctg gtc tac ggc gtg cac agc ctc ccg gtc      1392
Pro Leu Arg Ser Asp Met Leu Val Tyr Gly Val His Ser Leu Pro Val
    450                 455                 460 gcc tgg gac tga                                                      1404
Ala Trp Asp
465

<210> SEQ ID NO 6
<211> LENGTH: 33
<212> TYPE: DNA
<213> ORGANISM: Artificial Sequence
<220> FEATURE:
<223> OTHER INFORMATION: Primer 1

<400> SEQUENCE: 6
catggatcct gaactgagtg aattgatatg caa                                  33

<210> SEQ ID NO 7
<211> LENGTH: 31
<212> TYPE: DNA
<213> ORGANISM: Artificial Sequence
<220> FEATURE:
<223> OTHER INFORMATION: Primer 2

<400> SEQUENCE: 7
cccaagcttc tacccccatca acgcctgtac c                                   31

<210> SEQ ID NO 8
<211> LENGTH: 53
<212> TYPE: DNA
<213> ORGANISM: Artificial Sequence
<220> FEATURE:
<223> OTHER INFORMATION: Primer 3

<400> SEQUENCE: 8
gtaagatcta aataaggagg aataacatat ggcgctgacc accaccggca ccg            53

<210> SEQ ID NO 9
<211> LENGTH: 29
<212> TYPE: DNA
<213> ORGANISM: Artificial Sequence
<220> FEATURE:
<223> OTHER INFORMATION: Primer 4

<400> SEQUENCE: 9
tcaggatcct cggcacggag tgccgcgta                                       29
```

```
<210> SEQ ID NO 10
<211> LENGTH: 32
<212> TYPE: DNA
<213> ORGANISM: Artificial Sequence
<220> FEATURE:
<223> OTHER INFORMATION: Primer 5

<400> SEQUENCE: 10
taacatatga actcagtcgc agaaattttt ga                                    32

<210> SEQ ID NO 11
<211> LENGTH: 32
<212> TYPE: DNA
<213> ORGANISM: Artificial Sequence
<220> FEATURE:
<223> OTHER INFORMATION: Primer 6

<400> SEQUENCE: 11
cgaactagtg gtcacttgac catgcaaaaa ct                                    32

<210> SEQ ID NO 12
<211> LENGTH: 30
<212> TYPE: DNA
<213> ORGANISM: Artificial Sequence
<220> FEATURE:
<223> OTHER INFORMATION: Primer 7

<400> SEQUENCE: 12
ccgactagta ccgaaacgct gtaccccgag                                       30

<210> SEQ ID NO 13
<211> LENGTH: 30
<212> TYPE: DNA
<213> ORGANISM: Artificial Sequence
<220> FEATURE:
<223> OTHER INFORMATION: Primer 8

<400> SEQUENCE: 13
cctggatcct catgagaacg tcaccggcag                                       30

<210> SEQ ID NO 14
<211> LENGTH: 29
<212> TYPE: DNA
<213> ORGANISM: Artificial Sequence
<220> FEATURE:
<223> OTHER INFORMATION: Primer 9

<400> SEQUENCE: 14
ggccatatga ccgaaacgct gtaccccga                                        29

<210> SEQ ID NO 15
<211> LENGTH: 28
<212> TYPE: DNA
<213> ORGANISM: Artificial Sequence
<220> FEATURE:
<223> OTHER INFORMATION: Primer 10

<400> SEQUENCE: 15
gcgactagta ccagccccac cggttccc                                         28

<210> SEQ ID NO 16
<211> LENGTH: 30
<212> TYPE: DNA
<213> ORGANISM: Artificial Sequence
<220> FEATURE:
<223> OTHER INFORMATION: Primer 11
```

<400> SEQUENCE: 16
ccgggatcct cagtcccagg cgaccgggag                             30

<210> SEQ ID NO 17
<211> LENGTH: 26
<212> TYPE: DNA
<213> ORGANISM: Artificial Sequence
<220> FEATURE:
<223> OTHER INFORMATION: Primer 12

<400> SEQUENCE: 17
gcgcatatga ccagccccac cggttc                                26

<210> SEQ ID NO 18
<211> LENGTH: 31
<212> TYPE: DNA
<213> ORGANISM: Artificial Sequence
<220> FEATURE:
<223> OTHER INFORMATION: Primer 13

<400> SEQUENCE: 18
accactagtg cgctgaccac caccggcacc g                          31

<210> SEQ ID NO 19
<211> LENGTH: 31
<212> TYPE: DNA
<213> ORGANISM: Artificial Sequence
<220> FEATURE:
<223> OTHER INFORMATION: Primer 14

<400> SEQUENCE: 19
gggagatctt caggcgctgc gcggcccat c                           31

<210> SEQ ID NO 20
<211> LENGTH: 31
<212> TYPE: DNA
<213> ORGANISM: Artificial Sequence
<220> FEATURE:
<223> OTHER INFORMATION: Primer 15

<400> SEQUENCE: 20
acccatatgg cgctgaccac caccggcacc g                          31

<210> SEQ ID NO 21
<211> LENGTH: 30
<212> TYPE: DNA
<213> ORGANISM: Artificial Sequence
<220> FEATURE:
<223> OTHER INFORMATION: Primer 16

<400> SEQUENCE: 21 gcccccata tggcgctgac caccaccggc                             30

<210> SEQ ID NO 22
<211> LENGTH: 30
<212> TYPE: DNA
<213> ORGANISM: Artificial Sequence
<220> FEATURE:
<223> OTHER INFORMATION: Primer 17

<400> SEQUENCE: 22
gccactagtt caggcgctgc gcggcccat                             30

<210> SEQ ID NO 23
<211> LENGTH: 27
<212> TYPE: DNA

-continued

```
<213> ORGANISM: Artificial Sequence
<220> FEATURE:
<223> OTHER INFORMATION: Primer 18

<400> SEQUENCE: 23
cggactagtc tactcgatca ccttgat                                              27

<210> SEQ ID NO 24
<211> LENGTH: 32
<212> TYPE: DNA
<213> ORGANISM: Artificial Sequence
<220> FEATURE:
<223> OTHER INFORMATION: Primer 19

<400> SEQUENCE: 24
cgcactagtc agtcccaggc gaccgggagg ct                                        32

<210> SEQ ID NO 25
<211> LENGTH: 106
<212> TYPE: PRT
<213> ORGANISM: Actinobacter sp. OC4

<400> SEQUENCE: 25
```

Met Gly Gln Ile Thr Phe Ile Ala His Asp Gly Ala Gln Thr Ser Val
1               5                   10                  15

Ala Ile Glu Ala Gly Lys Ser Leu Met Gln Leu Ala Val Glu Asn Gly
            20                  25                  30

Val Ala Gly Ile Asp Gly Asp Cys Gly Gly Glu Cys Ala Cys Gly Thr
        35                  40                  45

Cys His Val Ile Val Ser Ala Glu Trp Ser Asp Val Ala Gly Thr Ala
    50                  55                  60

Gln Ala Asn Glu Gln Gln Met Leu Glu Met Thr Pro Glu Arg Ala Ala
65                  70                  75                  80

Thr Ser Arg Leu Ala Cys Cys Ile Gln Val Thr Asp Ala Met Asp Gly
                85                  90                  95

Met Thr Val His Leu Pro Glu Phe Gln Met
            100                 105

```
<210> SEQ ID NO 26
<211> LENGTH: 404
<212> TYPE: PRT
<213> ORGANISM: Actinobacter sp. OC4

<400> SEQUENCE: 26
```

Met Gln Thr Ile Val Ile Ile Gly Ala Ser His Ala Ala Ala Gln Leu
1               5                   10                  15

Ala Ala Ser Leu Arg Pro Asp Gly Trp Gln Gly Glu Ile Val Val Ile
            20                  25                  30

Gly Asp Glu Pro Tyr Leu Pro Tyr His Arg Pro Pro Leu Ser Lys Thr
        35                  40                  45

Phe Leu Arg Gly Ala Gln Leu Val Asp Glu Leu Leu Ile Arg Pro Ala
    50                  55                  60

Ala Phe Tyr Gln Lys Asn Gln Ile Glu Phe Arg His Gly Arg Val Val
65                  70                  75                  80

Ala Ile Asp Arg Ala Ala Arg Ser Val Thr Leu Gln Asp Gly Ser Thr
                85                  90                  95

Leu Ala Tyr Asp Gln Leu Ala Leu Cys Thr Gly Ala Arg Val Arg Thr
            100                 105                 110

Val Ser Leu Ala Gly Ser Asp Leu Ala Gly Val His Tyr Leu Arg Asn
        115                 120                 125

```
Ile Ser Asp Val Gln Ala Ile Gln Pro Phe Val Gln Pro Asn Gly Lys
    130                 135                 140

Ala Val Val Ile Gly Gly Tyr Ile Gly Leu Glu Thr Ala Ala Ala
145                 150                 155                 160

Leu Thr Glu Gln Gly Met Gln Val Val Leu Glu Ala Ala Glu Arg
                165                 170                 175

Ile Leu Gln Arg Val Thr Ala Pro Glu Val Ser Asp Phe Tyr Thr Arg
            180                 185                 190

Ile His Arg Glu Gln Gly Val Thr Ile His Thr Gly Val Ser Val Thr
        195                 200                 205

Ala Ile Thr Gly Glu Gly Arg Ala Gln Ala Val Leu Cys Ala Asp Gly
    210                 215                 220

Ser Met Phe Asp Ala Asp Leu Val Ile Ile Gly Val Gly Val Val Pro
225                 230                 235                 240

Asn Ile Glu Leu Ala Leu Asp Ala Gly Leu Gln Val Asp Asn Gly Ile
                245                 250                 255

Val Ile Asp Glu Tyr Cys Arg Thr Ser Ala Pro Glu Ile Val Ala Ile
            260                 265                 270

Gly Asp Cys Ala Asn Ala Phe Asn Pro Ile Tyr Gln Arg Arg Met Arg
        275                 280                 285

Leu Glu Ser Val Pro Asn Ala Asn Glu Gln Ala Lys Ile Ala Ser Ala
    290                 295                 300

Thr Leu Cys Gly Leu Gln Arg Thr Ser Lys Ser Leu Pro Trp Phe Trp
305                 310                 315                 320

Ser Asp Gln Tyr Asp Leu Lys Leu Gln Ile Ala Gly Leu Ser Gln Gly
                325                 330                 335

Tyr Asp Gln Ile Val Ile Arg Gly Asp Val Gln Arg Arg Ser Phe
            340                 345                 350

Ala Ala Phe Tyr Leu Gln Ala Gly Arg Leu Ile Ala Ala Asp Cys Val
        355                 360                 365

Asn Arg Pro Gln Glu Phe Met Leu Ser Lys Lys Leu Ile Thr Ala Gly
    370                 375                 380

Thr Ala Val Asp Pro Leu Arg Leu Ala Asp Glu Ser Ile Ala Val Gln
385                 390                 395                 400

Ala Leu Met Gly
```